(12) United States Patent
Phillion

(10) Patent No.: US 6,924,396 B2
(45) Date of Patent: Aug. 2, 2005

(54) α-HALOENAMINE REAGENTS

(75) Inventor: Dennis P. Phillion, St. Charles, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/664,123

(22) Filed: Sep. 17, 2003

(65) Prior Publication Data

US 2004/0092770 A1 May 13, 2004

Related U.S. Application Data

(63) Continuation of application No. 10/061,617, filed on Feb. 1, 2002, now Pat. No. 6,677,487.
(60) Provisional application No. 60/316,151, filed on Aug. 30, 2001.

(51) Int. Cl.$^7$ ............................................. C00C 211/15

(52) U.S. Cl. ....................... 564/510; 564/509; 562/840; 549/483; 549/484; 548/562

(58) Field of Search ................................. 564/509, 510; 562/840; 548/562; 549/483, 484

(56) References Cited

U.S. PATENT DOCUMENTS

| | | | |
|---|---|---|---|
| 4,216,172 A | 8/1980 | Heine et al. | |
| 4,291,176 A | 9/1981 | Heine et al. | |
| 4,794,109 A | 12/1988 | Lang | |
| 4,914,196 A | 4/1990 | Riediker et al. | |
| 5,218,097 A | 6/1993 | Ernst | |
| 5,273,991 A | 12/1993 | Lee | |
| 5,459,131 A | 10/1995 | Albright et al. | |
| 5,516,662 A | 5/1996 | Singh | |
| 5,643,878 A | 7/1997 | Bold et al. | |
| 6,677,487 B2 * | 1/2004 | Phillion | ...................... 564/510 |

FOREIGN PATENT DOCUMENTS

| | | |
|---|---|---|
| CH | 681623 A | 4/1993 |
| EP | 0639574 A1 | 2/1995 |
| GB | 2310207 A | 8/1997 |
| WO | WO 96/33972 A | 10/1996 |
| WO | WO 97/30975 A2 | 8/1997 |
| WO | WO 97/49395 A1 | 12/1997 |
| WO | WO 99/41367 A1 | 8/1999 |
| WO | WO 00/62778 A1 | 10/2000 |

OTHER PUBLICATIONS

S. Abel et al. "Total Synthesis of Soraphen $A_{1\alpha}$" Synthesis, vol. 1 (1999) pp. 188–197.*
Baird et al. "Solid Phase Synthesis of Polyamides Containing Imidazole and Pyrrole Amino Acids" J. Am. Chem. Soc., vol. 118, No. 26 (1996) pp. 6141–6146.
R. Banteli et al. "Synthesis of Sialyl Lewis Mimics. Modifications of the 6–Position of Galactose" Bioorganic & Medicinal Chemistry Letters, vol. 11 (2001) pp. 459–462.

J. Bendall et al. "Introduction of Bromine and Chlorine Substituents in Medium Ring Ethers and Lactones" Chem. Commun., Chem. Commun., vol. 11 (1997) pp. 1067–1068.
C. Blackburn "Polymer Supports for the Solid–Phase Organic Synthesis" Biopolymers (Peptide Science) vol. 47 (1998) pp. 311–351.
A. Cutler et al. "Chemistry of Dicarbonyl $n^5$–Cyclopentadienyl–$n^1$–alkyl– and $n^2$–olefiniron Complexes. Preparation and Cycloaddition Reactions" J. Am. Chem. Soc., vol. 98, No. 12 (1976) pp. 3495–3507.
Devos et al. "Synthesis of Acyl Halides Under Very Mild Conditions" J.C.S. Chem. Comm., vol. 1050 (1979) pp. 1180–1181.
A. De Mesmaeker et al. "A New Protected From of Glucuronic Acid for the Synthesis of Labile 1–O–acyl–β–D–glucuronides" Tetrahedron Letters, vol. 30, No. 29 (1989) pp. 3773–3776.
T. Durand et al. "Cyclopentenones as Potential Inhibitors of Penicillin Sensitive Enzymes" Bioorganic & Medicinal Chemistry Letters, vol. 3, No. 11 (1993) pp. 2309–2312.
E. Egert et al. "Stereoselective Synthesis of Functionalized, Tetra– and Penta–Substituted 1,3–Butadienes by Aliene Claisen Rearrangement" Tetrahedron Letters, vol. 28, No. 7 (1987) pp. 789–792.
D. Enders et al. "A Novel Approach to 2–Amino–1, 3–Dienes by Coupling of α–Chloro Enamines and Alkenyl Lithium Compounds" Tetrahedron, vol. 52, No. 8 (1996) pp. 2909–2924.
B. Ernst et al. "Haloenamines –II. A Rapid and Efficient Synthesis of Carbohydrate 1,2–Orthoesters" Tetrahedron Letters, vol. 31, No. 43 (1990) pp. 6167–6170.
B. Ernst et al. "Preparation of Glycosyl Halides Under Neutral Conditions" Tetrahedron Letters, vol. 30, No. 23 (1989) pp. 3081–3084.
T. Fujisawa et al. "A Convenient Coupling Reaction of Allyl Alcohols with Grignard Reagents Using 1–Chloro–2–Methyl–N,N–Tetramethylenepropenylamine" Tetrahedron Letters, vol. 24, No. 51 (1983) pp. 5745–5748.
T. Fujisawa et al. "A Convenient Synthesis of Allenes by the Reaction of Propargyl Alcohols with Grignard Reagents Using 1–Chloro–2–Methyl–N,N–Tetramethylenepropenylamine" Tetrahedron Letters, vol. 25, No. 36 (1984) pp. 4007–4010.
A. Furstner et al. "Total Synthesis of Caloporoside" J. Org. Chem., vol. 63, No. 9 (1998) pp. 3072–3080.
A. Furstner et al. "Total Synthesis of Roseophilin" J. Am. Chem. Soc., vol. 120, No. 12 (1998) pp. 2817–2825.
L. Ghosez et al. "A General and Practical Method of Synthesis of 2–disubstituted–1–chloro– and 1–bromoenamines" Tetrahedron, vol. 54 (1998) pp. 9207–9222.

(Continued)

Primary Examiner—Shailendra Kumar
(74) Attorney, Agent, or Firm—Senniger Powers

(57) ABSTRACT

The present invention describes immobilized haloenamine reagents, immobilized tertiary amides, methods for their preparation, and methods of use.

19 Claims, No Drawings

OTHER PUBLICATIONS

L. Ghosez et al. "Alkyl and Aryl α–Chloro Enamines" Angew. Chem. Internat. Edit., vol. 8, No. 6 (1969) pp. 454–455.

G. Guillier et al. "Linkers and Cleavage Strategies in Solid Phase Organic Synthesis and Combinatorial Chemistry" Chem. Rev., vol. 100, No. 6 (2000) pp. 2091–2157.

C. Hall et al. "Stereospecific Halogenation of Ethyl Methyl Phosphorothioic Acid" Tetrahedron Letters, vol. 23, No. 9 (1982) pp. 999–1002.

T. Harris et al. "Substituent Modification in Tri–O–Thymotide and its Effects on Host Geometry and Guest Enclathration .1. Synthesis" Tetrahedron, vol. 43, No. 7 (1987) pp. 1519–1540.

C. Harwig et al. "Soluble Polymers: New Options in Both Traditional and Combinatorial Synthesis" Chemtracts—Organic Chemistry, Soluble Polymers, vol. 12, No. 1 (1999) pp. 1–26.

R. Hoffmann et al. "Total Synthesis of Mycinolide–V" Liebigs Ann. Chem. (1990) pp. 23–29.

Houben–Weyl "Methoden der Organischen Chemie" vol. E5 (1985) "Carbhonsauren und Carbonsaure–Derivate" Georg Thieme Verlag, Suttgart, pp. 593–600.

C. Houge et al. "Models for Asymmetric [2 + 2] Cycloadditons" J. Am. Chem. Soc., vol. 104 (1982) pp. 2920–2921.

I. James "Linkers for Solid Phase Organic Synthesis" Tetrahedron, vol. 55 (1999) pp. 4855–4946.

M. Kazankova et al. "Nickel– and Palladium–Catalyzed Cross–Coupling as a Route to 1– and 2–Alkoxy– or Dialkylaminovinylphosphonates" Tetrahedron Letters, vol. 40 (1999) pp. 569–572.

M. Kazankova et al. "Synthesis of Vinyldiphenylphosphines by Pd–Catalyzed Cross–Coupling Reactions of Dipheylphosphine with Alkenylhalides" Tetrahedron Letters, vol. 39 (1998) pp. 573–576.

R. King et al. "Keteneimmonium and 2–Azabutadiene Complexes from Reactions of α–Chloroenamines with Metal Carbonyl Anions" J. Am. Chem. Soc., vol. 96, No. 4 (1974) pp. 1263–1264.

R. King et al. "Organonitrogen Derivatives of Metal Carbonyls VIII: Reactions of Metal Carbonyl Anions with α–Chloroenamines" J. of Am. Chem. Soc., vol. 97, No. 10 (1975) pp. 2702–2712.

B. Konig et al. "Synthesis of DNA–binding Heteroaromatic Oligoamides on Liquid Solid Support" Chem. Commun., No. 5 (1998) pp. 605–606.

K. Krowicki et al. "Synthesis of Novel Imidazole–Containing DNA Minor Groove Binding Oligopeptides Related to the Antiviral Antibiotic Netropsin" J. of Organic Chem., vol. 52, No. 16 (1987) pp. 3493–3501.

Manetti et al. "Synthesis and Binding Mode of Heterocyclic Analogues of Suramin Inhibiting the Human Basic Fibroblast Growth Factor" Bioorganic & Medicinal Chemistry, vol. 6, No. 7 (1998) pp. 947–958.

J. Marchand–Brynaert et al. "Cycloadditions of Keteneimmonium Cations to Olefins and Dienes. A New Synthesis of Four–Membered Rings" J. Am. Chem. Soc., vol. 94, No. 8 (1972) pp. 2870–2872.

J. Marchand–Brynaert et al. "Electrophilic Aminoalkenylation of Aromatics with α–Chloroenamines" J. Am. Chem. Soc., vol. 94, No. 8 (1972) pp. 2869–2870.

Marsham et al. "Quinazoline Antifolate Thymidylate Synthase Inhibitors: Heterocyclic Benzoyl Ring Modifications" J. Med. Chem., vol. 34, No. 5 (1991) pp. 1594–1605.

F. Munyemana et al. "Synthesis of Alkyl Halides Under Neutral Conditions" Tetrahedron Letters, vol. 30, No. 23 (1989) pp. 3077–3080.

P. Ortiz De Montellano et al. "Phenyl Substituted Cyclobutanones as Squalene Synthetase Inhibitors" Tetrahedron Letters, vol. 46 (1976) pp. 4115–4118.

PCT Search report for application No. PCT/US02/27953 dated Mar. 24, 2003.

PCT Search report for application No. PCT/US02/25609 dated Dec. 5, 2002.

H. Saimoto et al. "Nonstereospecificity in the Cycloadditions of Keteneiminium Salts to Olefins. Evidence for a Stepwise Mechanism" Tetrahedron Letters, vol. 24, No. 22 (1983) pp. 2251–2254.

E. Schaumann et al. "Cycloaddition Reactions of Sulfonylisothiocyanates with β,β–Disubstituted Enamines" Tetrahedron, vol. 30 (1974) pp. 4147–4152.

U. Schmidt et al. "Amino Acids and Peptides; 67. Easy Preparation and Use of Benzyloxycarbonyl Derivatives of Amino Acid Chlorides and α–Hydroxycarboxylic Acid Chlorides" Synthesis, vol. 6 (1988) pp. 475–477.

Schmidt et al. "Reaction Rate of p–nitrophenyl Acetate Hydrolysis Catalyzed by Histidine Derivatives and Peptides" Z. Physiol. Chem., vol. 345, No. 1 (1966) pp. 91–99 (Chem Abstracts).

A. Singh et al. "Phosphatidylhydroxyalkanols as Versatile Intermediates in the Synthesis of Headgroup Modified Diacetylenic Phsopholipids" Synthetic Communications, vol. 22, No. 16 (1992) pp. 2293–2304.

L. Tietze et al. "Preparation of a New Carboranyl Lactoside for the Treatment of Cancer by Boron Neutron Capture Therapy: Synthesis and Toxicity of Fluoro Carboranyl Glycosides for in vivo $^{19}$F–NMR Spectroscopy" Chem. Eur. J., vol. 6, No. 5 (2000) pp. 836–842.

A. Togni et al. "A New Entry into Sulfur Containing Ferrocenylphosphine Ligands for Asymmetric Catalysis" Synlett. (1990) pp. 633–635.

J. Toye et al. "Synthesis and Reactivity of α–Cyanoenamines. A Novel General Method for Preparing α–Diketones from Amides" J. Am. Chem. Soc., vol. 97, No. 8 (1975) pp. 2276–2277.

L. Van Hijfte et al. "A Versatile Entry into the Synthesis of α(Monofluoromethyl) Amino Acids: Preparation of α–(Monofluoromethyl) Serine and (E)–Dehydro–α–(monofluoromethyl) Ornithine" Tetrahedron Letters, vol. 34, No. 30 (1993) pp. 4793–4796.

H. Weingarten "Formation of an α–Chlorovinylamine and its Interconversion to a Ketenimmonium Salt" J. Org. Chem., vol. 35, No. 11 (1970) pp. 3970–3971.

S. Wendeborn et al. "Replacement of the Phosphodiester Linkage in Oligonucleotides by a C=C Double Bond: Comparison of the cis and trans Isomers" Tetrahedron Letters, vol. 36, No. 38 (1995) pp. 6879–6882.

T. Ziegler et al. "Synthetic Studies Toward Pyruvate Acetal Containing Saccharides. Synthesis of the Carbohydrate Part of the *Mycobacterium smegmatis* Pentasaccharide Glycolipid and Fragments Thereof for the Preparation of Neoantigens" J. Org. Chem., vol. 58, No. 5 (1993) pp. 1090–1099.

\* cited by examiner

α-HALOENAMINE REAGENTS

REFERENCE TO RELATED APPLICATIONS

This application is a continuation of U.S. application Ser. No. 10/061,617, filed Feb. 1, 2002 now U.S. Pat. No. 6,677,487, which claims priority from U.S. provisional application Ser. No. 60/316,151, filed on Aug. 30, 2001. The entire contents of both of these applications are incorporated herein by reference.

BACKGROUND OF THE INVENTION

The present invention relates in general to the field of α-haloenamine chemistry, processes for the preparation of α-haloenamines and, in one embodiment, to α-haloenamine reagents supported by an organic or inorganic material which, under a defined set of conditions, renders the supported reagent sufficiently insoluble to enable separation of the reagent from a mixture.

α-Haloenamine reagents are used in a number of synthetic reactions. For example, they are used to convert carboxylic acids to acid halides, alcohols to halides, sugars to sugar halides, and thiophosphoryl compounds to the corresponding phosphoryl halides. α-haloenamine reagents offer advantages over other reagents for such conversions, particularly under neutral conditions and in those instances in which the substrate for the reaction contains one or more sensitive functionalities.

Despite these advantages, haloenamines are not being used to their full potential for a variety of reasons. Among these reasons are synthetic challenges. Ghosez et al. (*Angew. Chem. Int. Ed. Engl.* 1969, 8, 454) disclosed a route which involved the reaction of tertiary amides with phosgene followed by the dehydrochlorination of the intermediate α-chloroiminium salts with triethylamine. According to Ghosez et al., the hazard associated with the use of large amounts of phosgene as well as the ban on phosgene in many laboratories led them to re-examine the preparation of β-disubstituted-α-chloroenamines; more recently, Ghosez et al. (*Tetrahedron* 54 (1998) 9207–9222) reported a synthetic route which was said to be conceptually the same as the previous one: it involved the reaction of a tertiary amide with a chlorinating agent followed by the elimination of hydrochloric acid from the resulting α-chloroiminium salt. The halogenating agents tried by Ghosez et al. were thionyl chloride, diphosgene, triphosgene, phosphorous oxychloride, and phosphorous oxybromide. Of these, only phosphorous oxychloride was said to be suitable for the preparation of large amounts of α-chloroenamines. Thionyl chloride was said to be unsuitable. Diphosgene and triphosgene were said to be suitable although in both cases aminor by-product was produced. As a result, Ghosez et al. stated that phosphorous oxychloride would probably supersede phosgene as the halogenating agent. Ghosez et al. also reported that they succeeded in preparing the corresponding α-bromoenamines which, until then, they said were only available by halide exchange. Despite the advances reported by Ghosez et al., the conversion of a tertiary amide to an α-chloroiminium salt, particularly when the nitrogen substituents are bulky can be difficult.

Recent advances in molecular biology, chemistry and automation have resulted in the development of rapid, high throughput screening (HTS) protocols to synthesize and screen large numbers of compounds for a desired activity or other desirable property in parallel. These advances have been facilitated by fundamental developments in chemistry, including the development of highly sensitive analytical methods, solid state chemical synthesis, and sensitive and specific biological assay systems. As a result, it is now common to carry out such reactions, in parallel, in a multi-well micro titer plate or other substratum having a plurality of wells for containing a reaction mixture, e.g., 96, 384 or even a greater number of wells. To date, however, α-haloenamine reagents have not been provided in a form which would enable rapid, automated use and purification from such reaction mixtures.

SUMMARY OF THE INVENTION

One aspect of the present invention, therefore, is an improved process for the preparation of α-haloenamines. The resulting α-haloenamines may be used in a wide variety of synthetic schemes, such as the conversion of hydroxy-containing compounds and thiol-containing compounds to the corresponding halides. If immobilized onto a support, the resulting α-haloenamines are particularly useful in high-throughput, automated and other systems where ease of separation is desired.

Briefly, therefore, the present invention is directed to a process for the preparation of an α-haloenamine. The process comprises combining a tertiary amide with a pentavalent phosphorous halide in a solvent to form an α-haloiminium salt and converting the α-haloiminium salt to the α-haloenamine with a base. The pentavalent phosphorous halide has the formula $P(X)_2(Z)_3$ 

wherein each X is independently a halogen atom and each Z is independently a halogen atom or a carbon atom which is part of a substituted or unsubstituted hydrocarbyl radical.

The present invention is further directed to such a process wherein the tertiary amide is optionally covalently linked to a support which enables physical separation of the α-haloenamine from a liquid composition.

Other aspects of the present invention will be in part apparent and in part pointed out hereinafter.

DETAILED DESCRIPTION OF THE PREFERRED EMBODIMENTS

A. Preparation of α-Haloenamines

In accordance with one aspect of the present invention, α-haloenamines may be prepared from tertiary amides and pentavalent phosphorous halides. The tertiary amide reacts with the pentavalent phosphorous halide to produce a haloiminium salt which is then converted to the α-haloenamine with a base.

In general, the tertiary amide may be any tertiary amide having a hydrogen atom bonded to the carbon which is in the alpha position relative to the carbonyl group of the tertiary amide and which does not interfere with the synthesis of or react with the α-haloenamine. In one embodiment, the tertiary amide has the general formula:

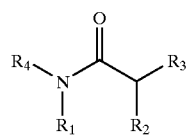

wherein $R_1$ and $R_4$ are independently hydrocarbyl, substituted hydrocarbyl, hydrocarbyloxy, or substituted hydrocarbyloxy; and $R_2$ and $R_3$ are independently hydrogen, hydrocarbyl, substituted hydrocarbyl, hydrocarbylthio, substituted hydrocarbylthio, hydrocarbylcarbonyl, substituted hydrocarbylcarbonyl, hydrocarbyloxycarbonyl, substituted hydrocarbyloxycarbonyl, phosphinyl, thiophosphinyl, sulfinyl, sulfonyl, halo, cyano, or nitro.

Ordinarily, it will be preferred that $R_2$ and $R_3$ are other than hydrogen, such as alkyl or aryl to increase the stability of the reagent to a variety of conditions. Nevertheless, under some circumstances, provided one of $R_2$ and $R_3$ is sufficiently electron-withdrawing, the other may be hydrogen. Under other circumstances, each of $R_2$ and $R_3$ is electron withdrawing. In no event, however, may $R_2$ and $R_3$ each be hydrogen.

In one embodiment of the present invention, one of $R_1$, $R_2$, $R_3$ and $R_4$ comprises a support which enables physical separation of the tertiary amide (or a derivative thereof) from a liquid mixture. The support may be, for example, any solid or soluble, organic or inorganic support which is conventionally used in chemical synthesis or any of a variety of assays. Such supports are described in greater detail elsewhere herein in connection with the supported α-haloenamine reagents of the present invention. Preferably, it is polystyrene or a derivative thereof, for example, a 1% cross linked polystyrene/divinyl benzene copolymer.

The pentavalent phosphorous-halide comprises at least two halogen atoms bonded to a pentavalent phosphorous atom. The three remaining valences are optionally occupied by bonds to carbon or halogen atoms. In general, therefore, the pentavalent phosphorous halide may be represented by the general formula $P(X)_2(Z)_3$ wherein each X is independently a halogen atom and each Z is independently a halogen atom or a carbon atom (which is part of a hydrocarbyl or substituted hydrocarbyl radical). For example, included within this general formula are pentavalent phosphorous halides in which the pentavalent phosphorous atom is bonded to two, three, four, or five halogen atoms selected from among chlorine, bromine and iodine. If fewer than five halogen atoms are bonded to the pentavalent phosphorous atom, the remaining valences are occupied by phosphorous-carbon bonds with the carbon being part of a hydrocarbyl or substituted hydrocarbyl radical, preferably phenyl or lower alkyl (e.g., methyl, ethyl or isopropyl). Although mixed halides are theoretically possible and within the scope of the present invention, for most applications it will generally be preferred that halogen atoms of only one type (e.g., only chlorine, bromine or iodine) be attached to the pentavalent phosphorous atom. Phosphorous pentachloride and phosphorous pentabromide are particularly preferred.

The α-haloiminium salt resulting from the reaction of the tertiary amide and the pentavalent phosphorous compound may be converted to the α-haloenamine with an amine base such as N,N-dialkyl anilines, trialkylamines, heterocyclic amines, pyridines, N-alkylimidazole, DBU and DBN. Tertiary amine bases such as triethylamine are generally preferred; other amine bases, however, such as substituted pyridines may be preferred under certain circumstances.

In general, therefore, and in accordance with one aspect of the present invention, α-haloenamines of the present invention may be prepared in accordance with the following reaction scheme:

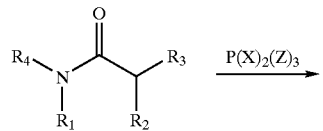

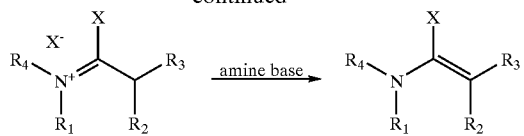

wherein
$R_1$ and $R_4$ are independently hydrocarbyl, substituted hydrocarbyl, hydrocarbyloxy, or substituted hydrocarbyloxy;
$R_2$ and $R_3$ are independently hydrogen, hydrocarbyl, substituted hydrocarbyl, hydrocarbylthio, substituted hydrocarbylthio, hydrocarbylcarbonyl, substituted hydrocarbylcarbonyl, hydrocarbyloxycarbonyl, substituted hydrocarbyloxycarbonyl, phosphinyl, thiophosphinyl, sulfinyl, sulfonyl, halo, cyano, or nitro, and
each X is independently chlorine, bromine or iodine; and
each Z is independently chlorine, bromine, iodine, hydrocarbyl or substituted hydrocarbyl.

The reaction may be carried out in acetonitrile, another solvent, or a mixture of solvents in which pentavalent phosphorous and the tertiary amide are sufficiently soluble. Other solvents include ethereal solvents (e.g., tetrahydrofuran, and 1,4-dioxane), esters (e.g., ethyl acetate), halogenated solvents (e.g., methylene chloride, chloroform and 1,2-dichloroethane), and under certain conditions, hydrocarbon solvents (e.g., toluene and benzene). If the solvent system comprises a mixture of solvents, the solvent system preferably comprises at least about 10% by weight, more preferably at least about 20% by weight acetonitrile.

If desired, the halogen atom, X, of the resulting α-haloenamine (e.g., the chlorine atom of α-chloroenamine or the bromine atom of α-bromoenamine) may be displaced by another halogen atom to form other α-haloenamine derivatives. Thus, for example, the chlorine atom of an α-chloroenamine may be displaced by a bromide, fluoride or iodide atom. Similarly, the bromine atom of an α-bromoenamine may be displaced by a fluoride or iodide atom. In general, the displacement may be carried out with an alkali metal halide (e.g., sodium, potassium, cesium or lithium bromide, fluoride or iodide).

B. Immobilized α-Haloenamine Reagents

The immobilized α-haloenamine reagent of the present invention comprises an α-haloenamine component tethered to a support which enables physical separation of the reagent from a liquid composition. The α-haloenamine component is tethered to the support by means of a linker and, optionally, a spacer. The immobilized α-haloenamine reagents of the present invention generally correspond to the formula

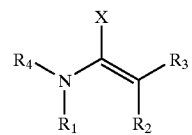

wherein X is halogen, and $R_1$, $R_2$, $R_3$ and $R_4$ are as previously defined provided, however, at least one of $R_1$, $R_2$, $R_3$ and $R_4$ comprises a support which enables physical separation of the reagent from a liquid composition. In general, reactivity tends to be greater when $R_1$, $R_2$, $R_3$ and $R_4$ are less bulky and when $R_1$, $R_2$, $R_3$ and $R_4$ are alkyl or aryl. Preferably, therefore, $R_1$, $R_2$, $R_3$ and $R_4$ are independently hydrocarbyl or substituted hydrocarbyl, more preferably hydrocarbyl, still more preferably alkyl or aryl, provided at least one of $R_1$, $R_2$, $R_3$ and $R_4$ comprises a support which enables physical separation of the reagent from a liquid composition.

In one embodiment, the α-haloenamine reagent support is a solid which is insoluble under all pertinent conditions. In another embodiment, the haloenamine reagent support is a composition which is selectively soluble in a solvent system; under a first set of conditions, the support is soluble but under a second set of conditions, the support is insoluble.

Insoluble polymers and other solid supports are typically the more convenient form since they may be easily separated from liquids by filtration. Such supports are routinely used in chemical and biochemical synthesis and include, for example, any insoluble inorganic or organic material that is compatible with chemical and biological syntheses and assays such as glasses, silicates, cross-linked polymers such as cross-linked polystyrenes, polypropylenes, polyacrylamides, polyacrylates and sand, metals, and metal alloys. For example, the α-haloenamine reagent support may comprise poly(N,N-disubstituted acrylamide), e.g., poly(N,N-dialkyl substituted acrylamide) or a copolymer thereof. Preferred materials include polystyrene-based polymers and copolymers. Commercially available materials include TentaGel resin and ArgoGel (Bayer), both polystyrene/divinylbenzene-poly(ethylene glycol) graft copolymers (with ~1–2% cross-linking) and 1% cross-linked polystyrene/divinylbenzene copolymer (ACROS) available in a range of particle sizes (e.g., 200–400 mesh).

In general, solid supports may be in the form of beads, particles, sheets, dipsticks, rods, membranes, filters, fibers (e.g., optical and glass), and the like or they may be continuous in design, such as a test tube or micro plate, 96 well or 384 well or higher density formats or other such micro plates and micro titer plates. Thus, for example, one, a plurality of, or each of the wells of a micro titer plate (96 well, 384 well or greater) or other multi well format substratum may have the α-haloenamine reagent of the present invention tethered to its surface. Alternatively, beads, particles or other solid supports having an α-haloenamine reagent of the present invention bound to its surface may be added to one, a plurality of, or each of the wells of a micro titer plate or other multi well substratum. Furthermore, if the solid support (whether in the form of a bead, particle, multi well micro titer plate, etc.) comprises poly(N,N-disubstituted acrylamide) or another polymer having tertiary amides chemically accessible at its surface, these tertiary amides may be converted to immobilized α-haloenamines of the present invention using a pentavalent phosphorous halide as otherwise described herein; stated another way, the source of the tertiary amide, from which the immobilized α-haloenamine of the present invention is derived may simply be a polymeric material comprising chemically accessible tertiary amides.

Solid-phase, polymer bound reagents, however, are not without their shortcomings. For example, phase differences obtained by heterogeneous, insoluble supports can create diffusion limitations due to the polymer matrix and this, in turn, can lead to reduced reactivity and selectivity as compared to classical, solution-phase synthesis. Furthermore, the insoluble nature of these supports can make synthesis and characterization of the polymer-reagent complex difficult. Accordingly, selectively soluble supports are preferred for some applications.

In general, any polymeric material which is soluble under one set of conditions and insoluble under a second set of conditions may be used as a selectively soluble support of the present invention provided this group does not interfere with the synthesis of or react with any of the reaction products or intermediates. Exemplary soluble polymers include linear polystyrene, polyethylene glycol, and their various polymers and copolymers derivatized with tertiary amides which may then be converted to α-haloenamines. In general, however, polyethylene glycol is preferred. Polyethylene glycol exhibits solubility in a wide range of organic solvents and water but is insoluble in hexane, diethyl ether, and tert-butyl methyl ether. Precipitation using these solvents or cooling of polymer solutions in ethanol or methanol yields crystalline polyethylene glycol which can be purified by simple filtration. Attaching a haloenamine group to the polyethylene glycol thus allows for homogeneous reaction conditions while permitting for relatively easy purification.

The α-haloenamine functionality or component of the α-haloenamine reagent is preferably attached to the support by means of a linker. The only requirement is that the linker be able to withstand the conditions of the reaction in which the haloenamine reagent will be employed. In one embodiment, the linker is selectively cleavable under a set of conditions to permit cleavage of the enamine from the support. In another embodiment, the linker is not.

A great number of cleavable linkers have been developed over the years to allow many multistep organic syntheses to be performed. These linkers have generally been classified into several major classes of cleavage reaction (with some overlap between classes): (a) electrophilically cleaved linkers, (b) nucleophilically cleaved linkers, (c) photocleavable linkers, (d) metal-assisted cleavage procedures, (e) cleavage under reductive conditions, and (f) cycloaddition- and cycloreversion-based release. See, e.g., Guillier et al., Linkers and Cleavage Strategies in Sold-Phase Organic Synthesis and Combinatorial Chemistry, *Chem. Rev.* 2000, 100, 2091–2157.

More typically, the linker is non-cleavable and merely constitutes a chain of atoms connecting the α-haloenamine to the solid support. The only requirement is that the sequence not react with any of the final products or intermediates. Thus, for example, any of the standard chemistries used to attach molecules to a solid support may be used to immobilize the α-haloenamine or, more preferably, a tertiary amide precursor which is then converted to the α-haloenamine using a pentavalent phosphorous halide. More specifically, a solid phase α-chloroenamine reagent may be derived from a polystyrene supported tertiary amide and $PCl_5$, with the polystyrene supported tertiary amide, in turn, being derived from polystyrene and a chloro-substituted tertiary amide in the presence of $FeCl_3$ (see Example 2). Alternatively, styrene (or another polymerizable monomer) having a tertiary amide as a substituent on the phenyl ring may be polymerized to form a polymer having a pendant tertiary amide which, as described elsewhere herein, may be converted to an α-haloenamine moiety using a pentavalent phosphorous halide, followed by treatment with a base.

Regardless of whether the linker is cleavable or non-cleavable, it may optionally include a spacer having a length and/or included moieties which provide the α-haloenamine reagent with more "solution-like" properties and better solvent compatibility. In general, the spacer group, if present, may be any atom, or linear, branched, or cyclic series of atoms which distance the α-haloenamine group from the support. The atoms, for example, may be selected from carbon, oxygen, nitrogen, sulfur and silicon. Preferred spacers include polyethylene glycol and alkyl chains.

In one embodiment of the present invention, one of $R_1$ and $R_4$ comprises a support and $R_2$, $R_3$ and the carbon atom to which they are attached are members of a carbocylic or heterocyclic ring:

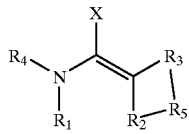

wherein $R_1$, $R_2$, $R_3$, $R_4$ and X are as previously defined and $R_5$ is an atom or chain of atoms, which together with $R_2$ and $R_3$ define a carbocyclic or heterocyclic structure. If the structure is heterocyclo, the hetero atoms are preferably selected from oxygen and sulfur; basic nitrogens are preferably not included as a ring atom. In addition, the atom or chain of atoms comprising $R_5$ may be substituted with one or more hydrocarbyl, substituted hydrocarbyl, hetero atom (s) or heterocyclo substituent. For example, together $R_2$, $R_3$, $R_5$ along with the carbon atom to which $R_2$ and $R_3$ are attached may comprise a cycloalkyl ring such as cyclopentyl or a five or six-membered heterocyclic ring. In another embodiment, $R_3$ comprises a support which enables physical separation of the reagent from a liquid composition, and any two of $R_1$, $R_2$, and $R_4$ and the atoms to which they are attached are members of a heterocyclic ring:

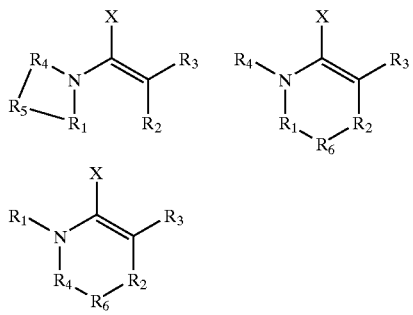

wherein $R_1$, $R_2$, $R_3$, $R_4$, and X are as previously defined and $R_5$ is an atom or a chain of atoms, and $R_6$ is a bond, an atom or chain of atoms, wherein $R_5$, together with $R_1$ and $R_4$, or $R_6$ together with $R_1$ and $R_2$, or $R_2$ and $R_4$ define a carbocyclic or heterocyclic structure. If the ring is heterocyclo, the hetero atoms are preferably selected from oxygen and sulfur; again, basic nitrogens are preferably not included as a ring atom. In each of these embodiments, $R_5$ preferably comprises two or three chain atoms selected from carbon, oxygen and sulfur, and $R_6$ is preferably a bond or an atom selected from carbon, oxygen and sulfur, thereby defining in each instance, a five or six membered heterocycle. In addition, the atom or chain of atoms or which $R_5$ and $R_6$ are comprised may optionally be substituted with one or more hydrocarbyl, substituted hydrocarbyl, hetero atom(s) or heterocyclo substituents.

C. Haloenamine Reactions

The α-haloenamines of the present invention and, in particular, the immobilized α-haloenamines of the present invention may be used in a variety of syntheses to convert hydroxy-containing and thiol-containing compounds to the corresponding halides. To avoid or at least minimize unwanted side reactions, the hydroxy or thiol-containing compounds preferably have an absence of other unprotected moieties which are also reactive with α-haloenamines. For example, basic primary and secondary amine moieties will react with α-haloenamines and thus, it is preferred that the hydroxy-containing or thiol-containing compound have an absence of unprotected basic primary and secondary amine moieties when it is reacted with an α-haloenamine of the present invention. Suitable protecting groups are identified, for example, in *Protective Groups in Organic Synthesis* by T. W. Greene and P. G. M. Wuts, John Wiley and Sons, 3rd ed. 1999.

In one embodiment, an immobilized α-haloenamine of the present invention is used to convert any of a wide range of carboxylic acids and thiocarboxylic acids to the corresponding acid halide. In a preferred embodiment, the carboxylic acids and thiocarboxylic acids have the formulae $R^{ca}COOH$ and $R^{ca}C(O)SH$ and the resulting corresponding halides have the formulae $R^{ca}COX$ wherein $R^{ca}$ is hydrogen, hydrocarbyl, substituted hydrocarbyl, or heterocyclo and X is halogen. For many applications, it will be preferred that X be chlorine or bromine, typically chlorine. In addition, $R^{ca}$ will often be alkyl, alkenyl, alkynyl, aryl, or heterocyclo optionally substituted with one or more substituents that do not react with the COX functionality or the haloenamine reagent, such as, one or more of halogen, heterocyclo, alkoxy, alkenoxy, alkynoxy, aryloxy, hydroxy (preferably on aryl or heteroaryl rings), protected hydroxy, formyl, acyl, acyloxy, amino, amido, nitro, cyano, thiol, sulfides, sulfoxides, sulfonamides, ketals, acetals, esters and ethers. For example, in one embodiment, X is chlorine or bromine, preferably chlorine, and $R^{ca}$ is heterocyclo. In general, however, it is preferred that compositions containing two carboxylic acid groups such as malonic acid be avoided since, upon reaction with an α-haloenamine, they may form a cyclic structure which may not be readily released. In another embodiment, an immobilized α-haloenamine of the present invention is used to convert any of a wide range of alcohols to the corresponding halides, provided the alcohol is not a substituent of a carbocyclic, aromatic ring. In a preferred embodiment, the alcohol corresponds to the formula $(R^a)_3COH$ wherein each $R^a$ is independently hydrogen, hydrocarbyl, substituted hydrocarbyl, or heterocyclo.

One particularly noteworthy class of alcohols which may be converted to the corresponding halides by reaction with immobilized α-haloenamines of the present invention are sugars. The conversion of a suitably protected sugar to the corresponding halide is depicted in the following reaction scheme:

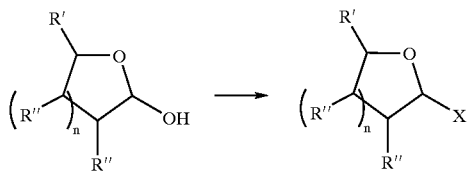

wherein
  X is F, Cl, or Br;
  each R" is independently H, OZ, NHZ, SZ, or at least one additional saccharide unit;
  R'=H, $(CH_2)_mOZ$, $(CH_2)_mNHZ$, or $(CH_2)_mSZ$, or at least one additional saccharide unit;
  m=0–1;
  n=1–2; and
  Z is a protecting group.

Thus, for example, the immobilized α-haloenamine of the present invention may be used to convert the hemiacetal alcohol moiety of a monosaccharide, a disaccharide or a polysaccharide to a halide. Exemplary monosaccharides include allose, altrose, arabinose, erythrose, fructose, galactose, glucose, gulose, idose, lyxose, mannose, psicose, ribose, ribulose, sorbose, tagatose, talose, threose, xylose, xylulose, and erythrulose. Other exemplary sugars include the deoxy analogs, such as deoxyribose, rhamnose and fucose.

In another embodiment, an immobilized α-haloenamine of the present invention is used to convert any of a wide range of silanols to the corresponding silyl halides. In a preferred embodiment, the silanol corresponds to the formula $(R^{si})_3SiOH$ and the resulting silyl halide corresponds to the formula $(R^{si})_3SiX$ wherein each $R^{si}$ is independently hydrogen, hydrocarbyl, substituted hydrocarbyl, hydrocarbyloxy, substituted hydrocarbyloxy, or heterocyclo, and X is halogen. For many applications, it will be preferred that X be chlorine or bromine, typically chlorine. In addition, $R^{si}$ will often be alkyl, alkenyl, alkynyl or aryl, optionally substituted with one or more moieties selected from halogen, heterocyclo, alkoxy, alkenoxy, alkynoxy, aryloxy, hydroxy (preferably on aryl or heteroaryl rings), protected hydroxy, formyl, acyl, acyloxy, amino, amido, nitro, cyano, thiol, sulfides, sulfoxides, sulfonamides, ketals, acetals, esters and ethers.

In another embodiment, an immobilized α-haloenamine of the present invention is used to convert any of a wide range of sulfonic or sulfinic acids to the corresponding sulfonyl or sulfinyl halide. In a preferred embodiment, the sulfonic or sulfinic acid corresponds to the formula $R^sS(=O)_nOH$, and the corresponding halide corresponds to the formula $R^sS(=O)_nX$ wherein $R^s$ is hydrocarbyl, substituted hydrocarbyl, or heterocyclo, X is halogen and n is 1 or 2. For many applications, it will be preferred that X be chlorine or bromine, typically chlorine. In addition, $R^s$ will often be alkyl, alkenyl, alkynyl or aryl, optionally substituted with one or more moieties selected from halogen, heterocyclo, alkoxy, alkenoxy, alkynoxy, aryloxy, hydroxy (preferably on aryl or heteroaryl rings), protected hydroxy, formyl, acyl, acyloxy, amino, amido, nitro, cyano, thiol, sulfides, sulfoxides, sulfonamides, ketals, acetals, esters and ethers.

In another embodiment, an immobilized α-haloenamine of the present invention is used to convert any of a wide range of phosphinic acids, phosphonic acids or phosphates (or the thio analogs thereof) to the corresponding phosphoryl halide. In a preferred embodiment, the phosphinic acid, phosphonic acid or phosphate corresponds to the formula $(R^P)_uP(O)(OH)_{3-u}$ and the corresponding halide corresponds to the formula $(R^P)_uP(O)X_{(3-u)}$ wherein each $R^P$ is hydrogen, hydrocarbyl, substituted hydrocarbyl, hydrocarbyloxy, substituted hydrocarbyloxy, or heterocyclo, X is halogen, and u is 0–2. In an alternative embodiment, the phosphinc acid, phosphonic acid or phosphate is a thio analog corresponding to the formula $(R^P)_uP(O)(ZH)_{3-u}$ and the corresponding halide corresponds to the formula $(R^P)_uP(=O)X_{(3-u)}$ wherein $R^P$, X, and u are as previously defined and Z is O or S with at least one Z being S. For many applications, it will be preferred that X be chlorine or bromine, typically chlorine. In addition, $R^P$ will often be alkyl, alkenyl, alkynyl or aryl, optionally substituted with one or more moieties selected from halogen, heterocyclo, alkoxy, alkenoxy, alkynoxy, aryloxy, hydroxy (preferably on aryl or heteroaryl rings), protected hydroxy, formyl, acyl, acyloxy, amino, amido, nitro, cyano, thiol, sulfides, sulfoxides, sulfonamides, ketals, acetals, esters and ethers. In general, however, it is preferred that phenylphosphinic acid $(C_6H_5H_2PO_2)$ be avoided since, upon reaction with an α-haloenamine, it forms a substance which is not readily released.

In another embodiment, an immobilized α-haloenamine of the present invention is used to dehydrate a non-aqueous solvent. The process comprises combining the solvent with an immobilized α-haloenamine reagent. The solvent may be any solvent which will not react with α-haloenamines.

F. Definitions

The terms "hydrocarbon" and "hydrocarbyl" as used herein describe organic compounds or radicals consisting exclusively of the elements carbon and hydrogen. These moieties include linear, branched or cyclic alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms. In addition, the hydrocarbyl moiety may be linked to more than one substitutable position of the tertiary amide or α-haloenamine of the present invention; for example, $R_2$ and $R_3$ of the tertiary amide or α-haloenamine may comprise the same chain of carbon atoms which, together with the carbon atoms to which $R_2$ and $R_3$ are attached define a carbocyclic ring.

The "substituted hydrocarbyl" moieties described herein are hydrocarbyl moieties which are substituted with at least one atom other than carbon; including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy (preferably on aryl or heteroaryl rings), protected hydroxy, formyl, acyl, acyloxy, amino, amido, nitro, cyano, thiol, sulfides, sulfoxides, sulfonamides, ketals, acetals, esters and ethers.

The term "heteroatom" shall mean atoms other than carbon and hydrogen.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, halogen, heterocyclo, alkoxy, alkenoxy, alkynoxy, aryloxy, hydroxy (preferably on aryl or heteroaryl rings), protected hydroxy, formyl, acyl, acyloxy, amino, amido, nitro, cyano, thiol, sulfides, sulfoxides, sulfonamides, ketals, acetals, esters and ethers. In addition, the heterocyclo moiety may be linked to more than one substitutable position of the tertiary amide or α-haloenamine of the present invention; for example, $R_1$ and $R_2$ of the tertiary amide or α-haloenamine may comprise the same chain of atoms which, together with the atoms to which $R_1$ and $R_2$ are attached define a heterocyclo ring.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, halogen, heterocyclo, alkoxy, alkenoxy, alkynoxy, aryloxy, hydroxy (preferably on aryl or heteroaryl rings), protected hydroxy, formyl, acyl, acyloxy, amino, amido, nitro, cyano, thiol, sulfides, sulfoxides, sulfonamides, ketals, acetals, esters and ethers.

The term "hydrocarbyloxy," as used herein denotes a hydrocaryl group as defined herein bonded through an oxygen linkage (——O——), e.g., RO— wherein R is hydrocarbyl.

"DBU" shall mean 1,8-diazabicyclo[5.4.0]undec-7-ene.
"DBN" shall mean 1,5-diazabicyclo[4.3.0]non-5-ene.
The following examples will illustrate the invention.

EXAMPLE 1

Improved Synthesis of N-(1-chloro-2-methylprop-1-enyl)-N,N-dimethylamine

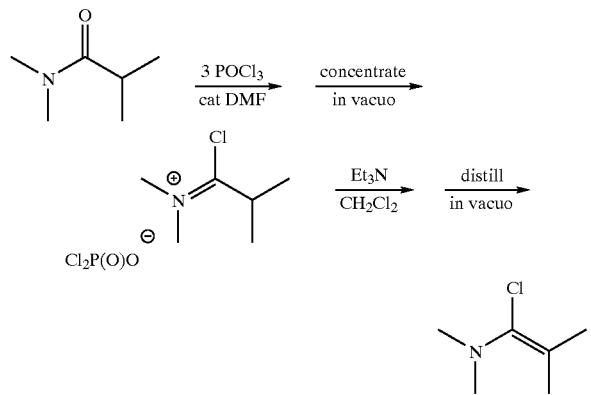

Dimethylisobutyramide (25.00 g, 217.39 mmol) was added dropwise over a 30-minute period to a solution of DMF (336 μL, 4.34 mmol) and $POCl_3$ (60.70 mL, 651.22 mmol). The resulting solution was stirred at ambient temperature and monitored by $^1$H-NMR. After 3 hours the reaction was concentrated under vacuum to remove all excess $POCl_3$. Triethylamine (33.30 mL, 238.91 mmol) was then added dropwise to a solution of the resulting chloroiminium salt dissolved in a small amount of $CH_2Cl_2$ (10 mL). This mixture was distilled at 70 C (100 Torr) to afford 22.70 g of N-(1-chloro-2-methylprop-1-enyl)-N,N-dimethylamine. $^1$H NMR ($CDCl_3$): δ 2.36 (s, 6H), 4.11 (s, 2H), 1.74 (br s, 6H).

EXAMPLE 2

Synthesis of N-(1-chloro-2-methylprop-1-enyl)-N-methyl aminomethylpolystyrene

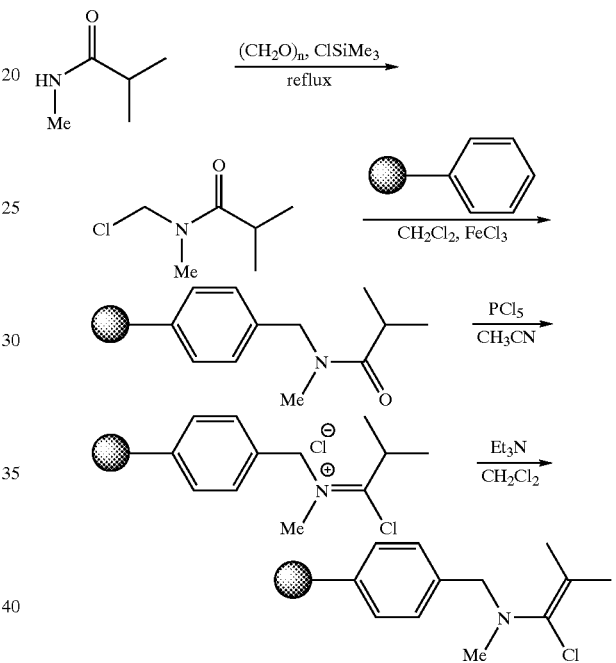

N-Chloromethyl-N-methyl isobutyramide: A mixture of N-methylisobutyramide (200.00 g, 1980 mmol) and paraformaldehyde (50.50 g, 1680 mmol) in chlorotrimethylsilane (860.40 g, 7920 mmol) was slowly heated to reflux. At about 62 C, the reaction exothermed and most of the paraformaldehyde dissolved. This mixture was refluxed for an additional 4 hours, and then was filtered to remove solids. This was concentrated to remove nearly all the excess TMSCl, and then again filtered to afford 219 g of N-chloromethyl-N-methylisobutyramide. $^1$H NMR ($CDCl_3$): (2 rotamers): δ 5.33 (s) and 5.30 (s) [2H combined], 3.11 (s) and 2.97 (s) [3H combined], 2.93 (heptet, J=6.2 Hz) and 2.75 (heptet, J=6.4 Hz) [1H combined], 1.14 (d, J=6.2 Hz) and 1.10 (d, J=6.2 Hz) [6H combined].

N-Methyl isobutyramidomethylpolystyrene: Anhydrous $FeCl_3$ (202.70 g, 1250 mmol) was added in portions to a mechanically stirred mixture of 1% crosslinked styrene-divinylbenzene copolymer (100 g, 960 mEq) and N-chloromethyl-N-methylisobutyramide (186.80 g, 1250 mmol) in $CH_2Cl_2$ (1L), maintaining the internal reaction temperature between −5° C. to 5° C. The resulting yellow slurry was stirred at room temperature for 5 days, and then was filtered and washed with CH$_2$Cl$_2$ (3×), 1:1 aqueous 1N HCl/1,4-dioxane (1×), and then with portions of MeOH until the color was gone. The 1:1 1 N HCl/1,4-dioxane wash step was very exothermic and controlled by 1$^{st}$ adding the 1,4-dioxane to the resin, and then cooling this stirred slurry with a dry ice/acetone bath while 1N HCl was added slowly. Vacuum drying at room temperature overnight afforded 193.0 g of the resin as an off-white solid. Amide loading on the resin was calculated to be 4.56 mmol/gm based on elemental analysis. Magic Angle $^{13}$C NMR (CD$_2$Cl$_2$): (2 rotamers): δ 177.38 and 176.95 (CO), 53.12 and 50.57 (CH$_2$N). 34.70 and 34.00 (NCH$_3$), 30.56 and 30.45 (CHMe$_2$), 20.03 and 19.53 (CH(CH$_3$)$_2$). FT-IR: 1642.92 cm$^{-1}$ (broad CO stretch). Anal. Calcd for 1.00 C$_{14}$H$_{19}$NO+ 0.10H$_2$O: C, 76.74; H, 8.83; N, 6.39; O, 8.03. Found: C, 76.65; H, 8.74; N, 6.30; O, 7.81.

N-(1-Chloro-2-methylprop-1-enyl)-N-methyl aminomethylpolystyrene: N-methyl isobutyramidomethylpolystyrene (100.00 g, 456 mEq) was washed twice with dry CH$_3$CN (@1.5L). A fresh portion of CH$_3$CN (1.5L) was then added, and the reaction was cooled with an ice-water bath while PCl$_5$ (330.16 g, 1585 mmol) was added in portions, at a rate which maintained the internal reaction temperature from 10° C. to 17° C. The resulting mixture was slowly stirred at room temperature for 4 hours, and then was filtered and washed with 2 portions of CH$_3$CN. The swelled polymer was compacted 3-fold by washing with 3 portions of CHCl$_3$ This CH$_3$CN/CHCl$_3$ cycle of washes was repeated to completely remove the excess PCl$_5$.

A slurry of this chloroiminium chloride of N-methyl isobutyramidomethylpolystyrene was prepared in anhydrous CHCl$_3$ (1.5 L). This was cooled with dry-ice/acetone to −10° C. while Et$_3$N (317 mL, 2275 mmol) was added dropwise. A precipitate of Et$_3$NHCl did not form. The resulting mixture was stirred at 0° C. for 2 hours, and then was filtered and washed sequentially with equal portions of CHCl$_3$, 1:2 CH$_3$CN/CHCl$_3$, 1:1 CH$_3$CN/CHCl$_3$, and then CHCl$_3$ Reaction solvents were anhydrous and the CHCl$_3$ was stabilized with amylenes. Vacuum drying afforded golden yellow N-(1-chloro-2-methylprop-1-enyl)-N-methyl aminomethylpolystyrene.

Resin loading was determined by adding excess acetic acid (26.9 mg) to a slurry of N-(1-chloro-2-methylprop-1-enyl)-N-methyl aminomethylpolystyrene (96 mg) in CDCl$_3$ (800 mL), and integrating the acetyl peaks in the $^1$H NMR spectrum after 10 minutes of stirring at room temperature. A value of 2.64 mEq/gm was calculated from [(CH$_3$COCl integral)/(CH$_3$COOH integral)]×26.9 mg/60.05/0.096 g.

EXAMPLE 3

Synthesis of 1-methyl-4-(BOC amino)pyrrole-2-carbonyl Chloride

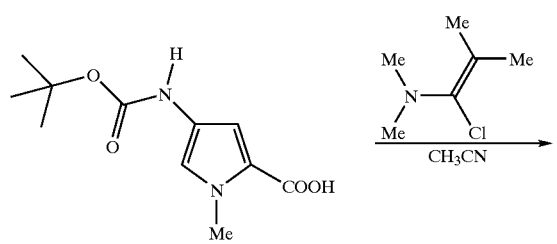

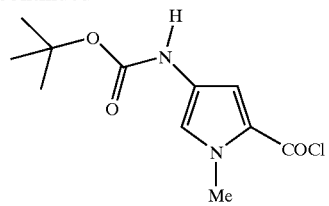

N-(1-chloro-2-methylprop-1-enyl)-N,N-dimethylamine (31 μL, 0.23 mmol) was added to a mixture of 1-methyl-4-(BOC amino)pyrrole-2-carboxylic acid (50 mg, 0.21 mmol) in CDCl$_3$ (200 mL). After a few minutes, the $^1$H-NMR of the reaction mixture showed complete conversion of the acid to the acid chloride. The proton spectrum of this solution of acid chloride did not change on standing overnight at room temperature. $^1$H NMR (CDCl$_3$): δ 7.35 (br s, 1H), 6.93 (d, J=2 Hz, 1H), 6.46 (br s, 1H), 3.82 (s, 3H), 1.50 (s, 9H).

EXAMPLE 4

Synthesis of 1-methyl-4-(BOC amino)imidazole-2-carbonyl Chloride

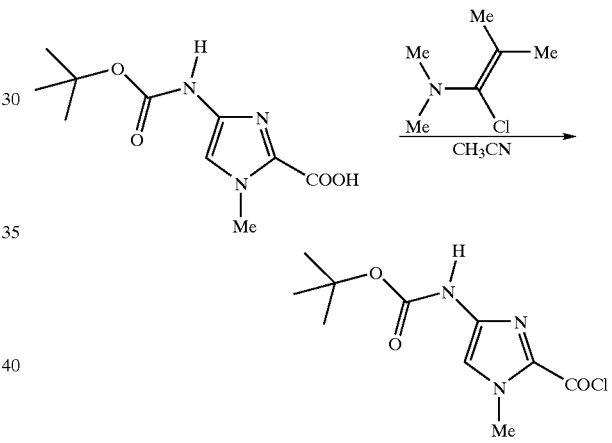

N-(1-chloro-2-methylprop-1-enyl)-N,N-dimethylamine (660 μL, 4.99 mmol) was added to a mixture of 1-methyl-4-(BOC amino)imidazole-2-carboxylic acid (1.00 g, 4.17 mmol) in CHCl$_3$ (8.00 mL). After a few minutes, the $^1$H-NMR of the reaction mixture showed complete conversion of the acid to the acid chloride. $^1$H NMR (CDCl$_3$): δ 7.48 (br s, 1H), 3.95 (s, 3H), 1.50 (s, 9H).

EXAMPLE 5

General Synthesis of Acid Chlorides Using N-(1-chloro-2-methylprop-1-enyl)-N-methyl aminomethylpolystyrene

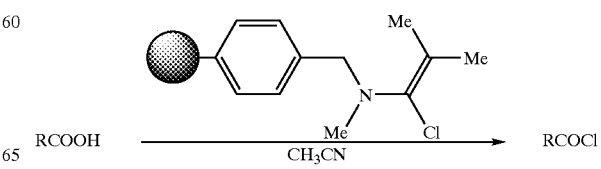

In a dry box, 2 equivalents of N-(1-chloro-2-methylprop-1-enyl)-N-methyl aminomethylpolystyrene was added to a stirred 0.20M–0.25M mixture of ~0.5–1.0 mmol of a carboxylic acid in $CD_3CN$. The resulting reaction mixture was monitored to completion by $^1$H-NMR. Aliquots of the liquid phase containing the acid chloride were then derivatized by addition to small volumes of methanol, ethanol, or aqueous 40% $MeNH_2$. These reactions were monitored to completion over 1–3 h by $^1$H-NMR and HPLC to form the ester or amide, and then were concentrated under vacuum and characterized. Reverse phase HPLC was carried out on an Agilent 1100 system using a Vydac 4.6×250 mm Protein & Peptide C18 column eluted at 1.2 mL/min with a linear gradient of 20% MeCN:80% $H_{2O}$ to 100% MeCN over a 15 minute period. Both solvents contained 0.1% TFA. The compounds of examples A–M were prepared by these procedures.

EXAMPLE 5A

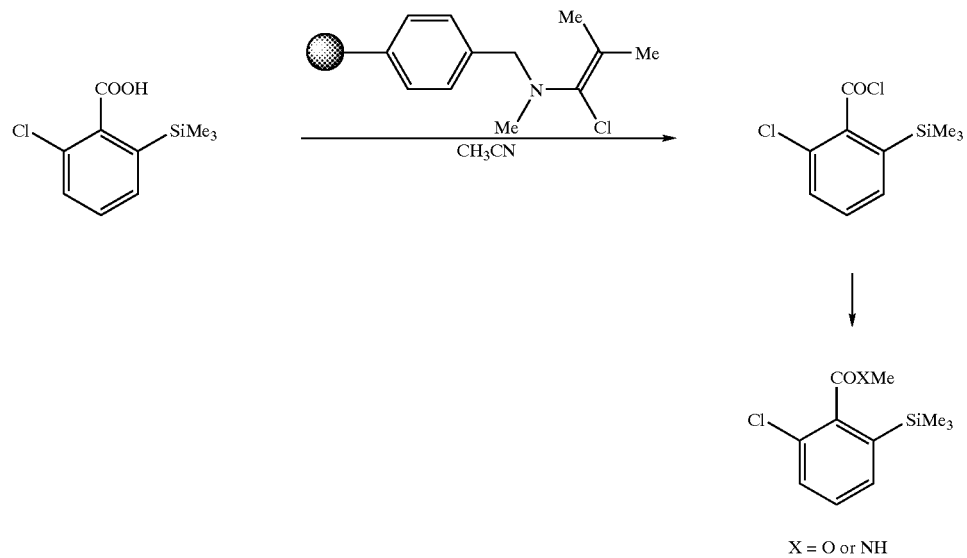

2-Chloro-6-trimethylsilanyl benzoyl chloride was cleanly and completely formed from 2-chloro-6-trimethylsilanyl benzoic acid within 1 h. $^1$H NMR ($CD_3CN$): δ 7.30–7.13 (m, 3H), 0.00 (s, 9H). $^{13}$C NMR ($CD_3CN$): δ 169.82 (CO), 142.34, 138.69, 133.82, 131.78, 130.75, 128.46, −1.04 (SiCH$_3$).

Methyl 2-chloro-6-trimethylsilanyl benzoate formed cleanly and completely from the reaction of 2-chloro-6-trimethylsilanyl benzoyl chloride with methanol, to afford a single 254 nm HPLC peak at 12.604 min. $^1$H NMR ($CD_3CN$): δ 7.32–7.13 (m, 3H), 3.63 (s, 3H), 0.00 (s, 9H). $^{13}$C NMR ($CD_3CN$): δ 168.70 (CO), 140.35, 138.45, 133.31, 130.60, 130.22, 52.22 (OCH$_3$), −1.44 (SiCH$_3$). GC-MS showed a single peak in the TIC: m/z 227 (M$^+$−Me).

N-Methyl-2-chloro-6-trimethylsilanyl benzamide formed cleanly and completely from the reaction of 2-chloro-6-trimethylsilanyl benzoyl chloride with aqueous 40% methylamine, to afford a single 254 nm HPLC peak at 8.417 min. $^1$H NMR ($CD_3CN$): δ 7.28–7.06 (m, 3H), 2.58 (d, J=4.83 Hz, 3H), 0.00 (s, 9H). $^{13}$C NMR ($CD_3CN$): δ 140.38, 133.27, 129.97, 129.66, 25.45 (NCH$_3$), −1.11 (SiCH$_3$). Calculated $C_{11}H_{17}ClNOSi$ (M$^+$+1) exact mass=242.0762. Found 242.0749.

EXAMPLE 5B

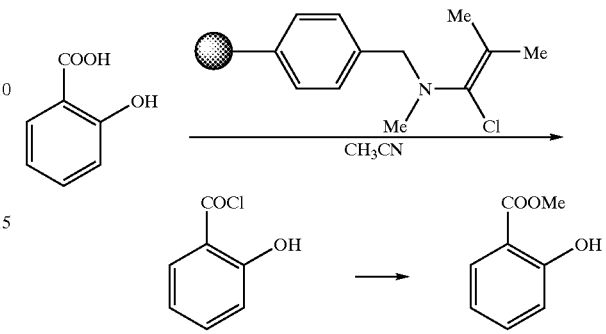

2-Hydroxy benzoyl chloride was cleanly and completely formed from 2-hydroxy benzoic acid within 15 min. $^1$H NMR ($CD_3CN$): δ 9.37 (s, 1H), 8.11 (dd, J=8.2 Hz, 1.7 Hz, 1H), 7.67 (d of t, J=7.8 Hz, 1.7 Hz, 1H), 7.11–7.04 (m, 2H). $^{13}$C NMR ($CD_3CN$): δ 172.42 (CO), 161.19, 138.76, 134.20, 120.75, 118.08.

Methyl 2-hydroxy benzoate was formed cleanly and completely from the reaction of 2-hydroxy benzoyl chloride with methanol, to afford a single 254 nm HPLC peak at 8.510 min. $^1$H NMR ($CD_3CN$): δ 10.66 (br s, 1H), 7.82 (dd, J=8.0 Hz, 1.7 Hz, 1H), 7.48 (d of t, J=7.8 Hz, 1.7 Hz, 1H), 6.94–6.89 (m, 2H), 3.89 (s, 3H). $^{13}$C NMR ($CD_3CN$): δ 170.70 (CO), 161.49, 136.04, 130.11, 119.58, 117.45, 112.71, 52.34 (OCH$_3$). GC-MS showed a single peak in the TIC: m/z 152 (M$^+$).

EXAMPLE 5C

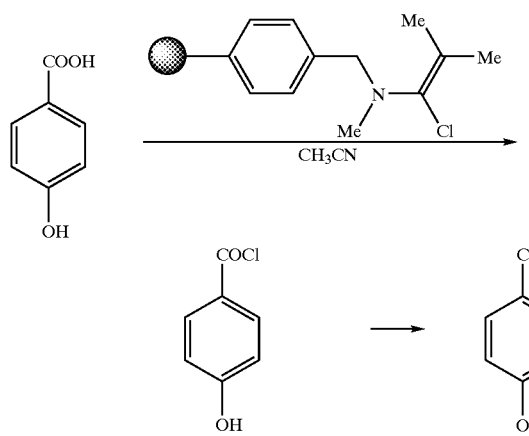

4-Hydroxy benzoyl chloride was cleanly and completely formed from 4-hydroxy benzoic acid within 15 min. $^1$H NMR (CD$_3$CN): δ 8.31 (br s, 1H), 8.02 (d, J=8.9 Hz, 2H), 6.99 (d, J=8.8 Hz, 2H). $^{13}$C NMR (CD$_3$CN): δ 164.18, 134.50, 116.13.

Methyl 4-hydroxy benzoate formed cleanly and completely from the reaction of 4-hydroxy benzoyl chloride with methanol, to afford a single 254 nm HPLC peak at 5.237 min. $^1$H NMR (CD$_3$CN): δ 7.88 (d, J=8.8 Hz, 2H), 6.88 (d, J=8.8 Hz, 2H), 3.82 (s, 3H). $^{13}$C NMR (CD$_3$CN): δ 166.65, 161.45, 131.69, 115.33, 51.49 (OCH$_3$).

N-Methyl 4-hydroxy benzamide formed cleanly and completely from the reaction of 4-hydroxy benzoyl chloride with aqueous 40% methylamine, to afford a broad 254 nm HPLC peak at 2.512 min. $^1$H NMR (CD$_3$CN): δ 7.66 (d, J=8.8 Hz, 2H), 7.51 (br s, 1H), 6.85 (d, J=8.6 Hz, 2H), 2.83 (d, J=4.7 Hz, 3H). $^{13}$C NMR (CD$_3$CN): δ 128.97, 115.07, 25.76 (NCH$_3$). Calculated C$_8$H$_{10}$NO$_2$ (M$^+$+1) exact mass=152.0706. Found 152.0602.

EXAMPLE 5D

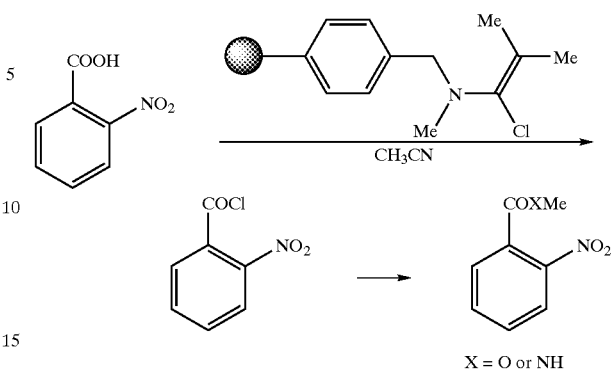

2-Nitrobenzoyl chloride was cleanly and completely formed from 2-nitrobenzoic acid within 20 min. $^1$H NMR (CD$_3$CN): δ 8.13 (d, J=2.4 Hz, 1H), 7.91–7.81 (m, 3H). $^{13}$C NMR (CD$_3$CN): δ 134.71, 133.89, 129.10, 125.00.

Methyl 2-nitrobenzoate formed cleanly and completely from the reaction of 2-nitrobenzoyl chloride with methanol, to afford a single 304 nm HPLC peak at 7.284 min. $^1$H NMR (CD$_3$CN): δ 7.94–7.92 (m, 2H), 7.79–7.69 (m, 3H), 3.87 (s, 3H). $^{13}$C NMR (CD$_3$CN): δ 165.89, 133.56, 132.62, 130.04, 127.18, 124.21, 53.05 (OCH$_3$).

N-Methyl-2-nitrobenzamide formed cleanly and completely from the reaction of 2-nitrobenzoyl chloride with aqueous 40% methylamine, to afford a broad 304 nm HPLC peak at 3.153 min. $^1$H NMR (CD$_3$CN): δ 7.96 (d, J=8.0 Hz, 1H), 7.74–78.53 (m, 3H), 6.94 (br s, 1H), 2.84 (d, J=4.8 Hz, 3H). $^{13}$C NMR (CD$_3$CN): δ 166.63, 133.70, 130.83, 128.95, 124.42, 25.97 (NCH$_3$). Calculated C$_8$H$_9$N$_2$O$_3$ (M$^+$+1) exact mass=181.0608. Found 181.0621.

EXAMPLE 5E

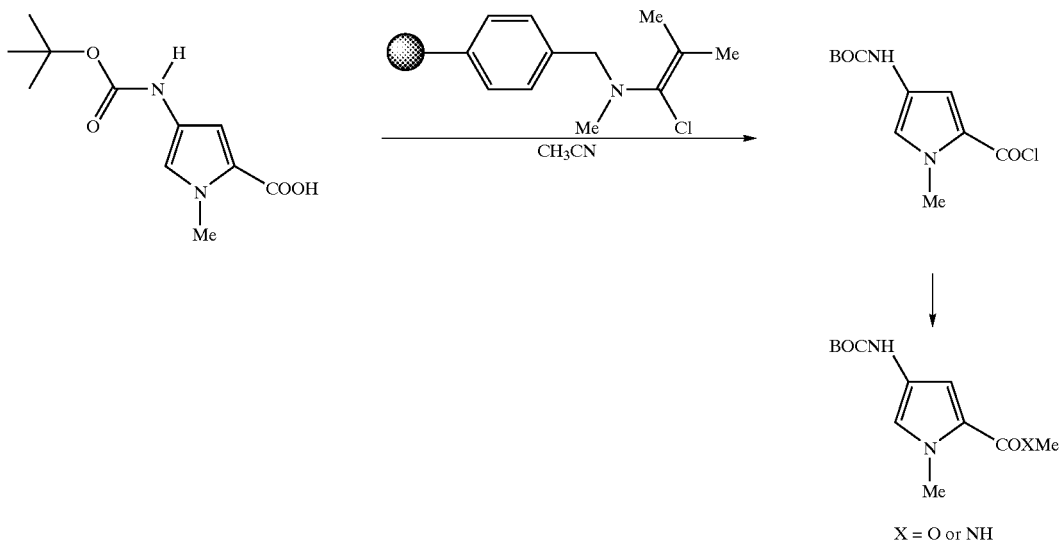

(5-Chlorocarbonyl-1-methyl-1 H-pyrrol-3-yl)-carbamic acid tert-butyl ester was cleanly and completely formed from 4-tert-butoxycarbonylamino-1-methyl-1H-pyrrole-2-carboxylic acid overnight. $^1$H NMR (CD$_3$CN): δ 7.35 (br s,1H), 7.03 (d, J=1.9 Hz, 1H), 3.79 (s, 3H), 1.47 (s, 9H). $^{13}$C NMR (CD$_3$CN): δ 156.20, 125.54, 114.59, 36.96, 27.69.

Methyl 4-tert-butoxycarbonylamino-1-methyl-1H-pyrrole-2-carboxylate formed cleanly and completely from the reaction of (5-chlorocarbonyl-1-methyl-1H-pyrrol-3-yl)-carbamic acid tert-butyl ester with methanol, to afford a single 304 nm HPLC peak at 8.547 min. $^1$H NMR (CD$_3$CN): δ 7.27 (br s, 1H), 7.03 (br s, 1H), 6.63 (s, 1H), 3.82 (s, 3H), 3.74 (s, 3H), 1.46 (s, 9H). $^{13}$C NMR (CD$_3$CN): δ 161.35, 153.37 123.07, 119.54, 107.68, 50.70 (OCH$_3$), 36.13, 27.73. Calculated C$_{12}$H$_{19}$N$_2$O$_4$ (M$^+$+1) exact mass=255.1339. Found 255.1333.

(1-Methyl-5-methylcarbamoyl-1H-pyrrol-3-yl)-carbamic acid tert-butyl ester formed cleanly and completely from the reaction of (5-chlorocarbonyl-1-methyl-1H-pyrrol-3-yl)-carbamic acid tert-butyl ester with aqueous 40% methylamine, to afford a single 304 nm HPLC peak at 5.870 min. $^1$H NMR (CD$_3$CN): δ 7.27, (br s, 1H), 6.82 (br s, 1H), 6.58 (br s, 1H), 6.45 (s, 1H), 3.81 (s, 3H), 2.76 (d, J=4.7 Hz, 3H), 1.46 (s, 9H). $^{13}$C NMR (CD$_3$CN): δ 162.25, 153.43, 122.49, 122.34, 102.76, 35.78, 35.75, 27.76, 25.09 (NCH$_3$). Calculated C$_{12}$H$_{20}$N$_3$O$_3$ (M$^+$+1) exact mass=254.1499. Found 254.1504.

EXAMPLE 5F

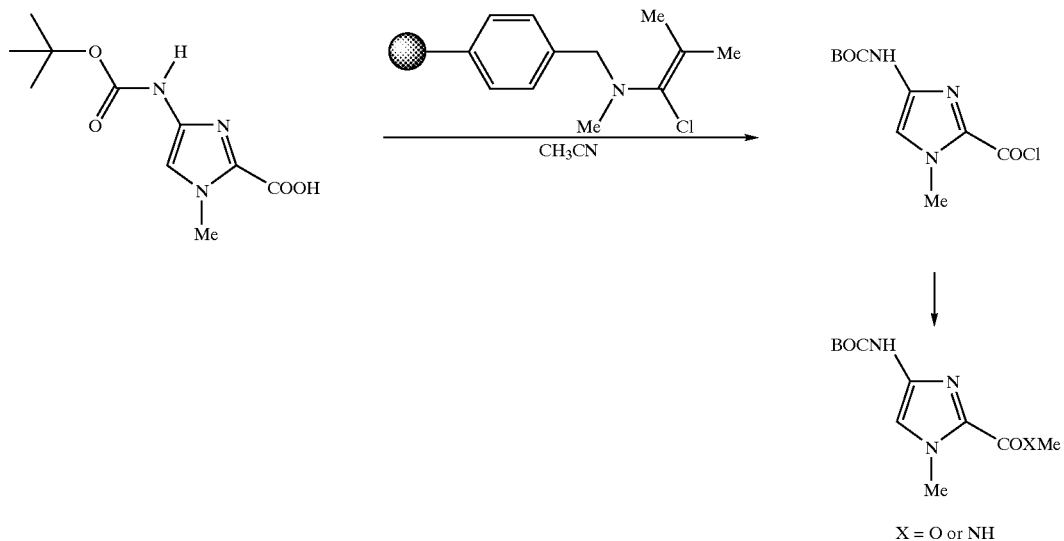

(2-Chlorocarbonyl-1-methyl-1H-imidazol-4-yl)-carbamic acid tert-butyl ester cleanly and completely formed from 4-tert-butoxycarbonylamino-1-methyl-1H-imidazole-2-carboxylic acid within 1 hour. $^1$H NMR (CD$_3$CN): δ 8.02 (br s, 1H), 7.50 (br s, 1H), 3.89 (s, 3H), 1.48 (s, 9H).

Methyl 4-tert-butoxycarbonylamino-1-methyl-1H-imidazole-2-carboxylate formed cleanly and completely from the reaction of (2-chlorocarbonyl-1-methyl-1H-imidazol-4-yl)-carbamic acid tert-butyl ester with methanol, to afford a single 304 nm HPLC peak at 6.088 min. $^1$H NMR (CD$_3$CN): δ 9.11 (br s, 1H), 7.35 (br s, 1H), 3.98 (s, 3H), 3.92 (s, 3H), 1.49 (s, 9H). Calculated C$_{11}$H$_{18}$N$_3$O$_4$ (M$^+$+1) exact mass=256.1292. Found 256.1291.

(1-Methyl-2-methylcarbamoyl-1H-imidazol-4-yl)-carbamic acid tert-butyl ester formed cleanly and completely from the reaction of (2-chlorocarbonyl-1-methyl-1H-imidazol-4-yl)-carbamic acid tert-butyl ester with aqueous 40% methylamine, to afford a single 304 nm HPLC peak at 5.642 min. $^1$H NMR (CD$_3$CN): δ 7.36, (br s, 1H), 7.04 (br s, 1H), 3.94 (s, 3H), 2.81 (s, 3H), 1.47 (s, 9H). Calculated C$_{11}$H$_{19}$N$_4$O$_3$ (M$^{30}$ +1) exact mass=255.1452. Found 255.1429.

EXAMPLE 5G

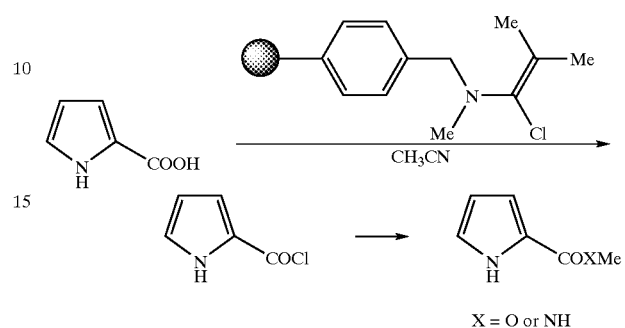

1H-Pyrrole-2-carbonyl chloride cleanly and completely formed from 1 H-pyrrole-2-carboxylic acid within 15 min. $^1$H NMR (CD$_3$CN): δ 7.26 (br m, 1H), 7.21 (br m, 1H), 6.37 (br m, 1H). $^{13}$C NMR (CD$_3$CN): δ 129.13, 122.80, 112.04.

Methyl 1H-pyrrole-2-carboxylate formed cleanly and completely from the reaction of 1H-pyrrole-2-carbonyl chloride with methanol, to afford a single 254 nm HPLC peak at 4.763 min. $^1$H NMR (CD$_3$CN): δ 9.98 (br m, 1H), 6.99 (s, 1H), 6.83 (s, 1H), 6.23 (m, 1H), 3.79 (s, 3H). $^{13}$C NMR (CD$_3$CN): δ 123.48, 115.00, 109.96, 50.96 (OCH$_3$). GC-MS showed a single peak in the TIC: m/z 125 (M$^+$).

N-Methyl-1H-pyrrole-2-carboxamide formed cleanly and completely from the reaction of 1H-pyrrole-2-carbonyl chloride with aqueous 40% methylamine, to afford a single 254 nm HPLC peak at 2.789 min. $^1$H NMR (CD$_3$CN): δ 9.89, (br s, 1H), 6.88 (m, 1H), 6.67 (br s, 1H), 6.59 (m, 1H), 6.17 (m, 1H), 2.81 (d, J=4.8 Hz, 3H). $^{13}$C NMR (CD$_3$CN): δ 121.17, 109.24, 108.97, 25.11 (NCH$_3$). Calculated C$_6$H$_9$N$_2$O (M$^+$+1) exact mass=125.0709. Found 125.0717.

EXAMPLE 5H

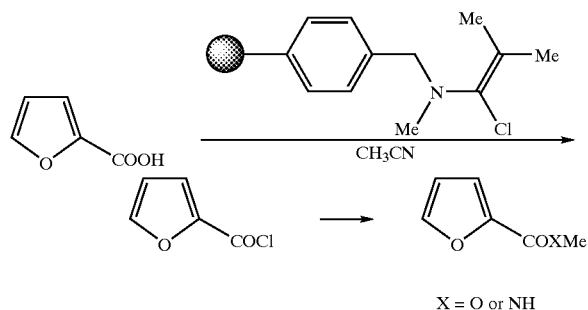

Furan-2-carbonyl chloride cleanly and completely formed from furan-2-carboxylic acid within 25 min. $^1$H NMR (CD$_3$CN): δ 7.93 (dd, J=1.0 Hz, 1.7 Hz, 1H), 7.63 (dd, J=0.7 Hz, 3.7 Hz, 1H), 6.74 (dd, J=1.7 Hz, 3.7 Hz, 1H). $^{13}$C NMR (CD$_3$CN): δ 151.39, 145.92, 125.82, 113.83.

Methyl furan-2-carboxylate formed cleanly and completely from the reaction of furan-2-carbonyl chloride with methanol, to afford a single 254 nm HPLC peak at 4.987 min. $^1$H NMR (CD$_3$CN): δ 7.70 (dd, J=0.8 Hz, 1.7 Hz, 1H), 7.20 (dd, J=0.8 Hz, 3.4 Hz, 1H), 6.59 (dd, J=1.8 Hz, 3.4 Hz, 1H), 3.83 (s, 3H). $^{13}$C NMR (CD$_3$CN): δ 159.04, 147.14, 144.78, 118.01, 112.13, 51.60 (OC̲H$_3$). GC-MS showed a single peak in the TIC: m/z 126 (M$^+$).

N-Methyl furan-2-carboxamide formed cleanly and completely from the reaction of furan-2-carbonyl chloride with aqueous 40% methylamine, to afford a single 254 nm HPLC peak at 2.662 min. $^1$H NMR (CD$_3$CN): δ 7.56, (dd, J=0.8 Hz, 1.7 Hz, 1H), 6.98 (dd, J=0.8 Hz, 3.4 Hz, 1H), 6.54 (dd, J=1.8 Hz, 3.5 Hz, 1H), 2.83 (d, J=4.8 Hz, 3H). $^{13}$C NMR (CD$_3$CN): δ 144.59, 113.00, 111.90, 25.05 (NC̲H$_3$). Calculated C$_6$H$_8$NO$_2$ (M$^+$+1) exact mass=126.0550. Found 126.0553.

EXAMPLE 5I

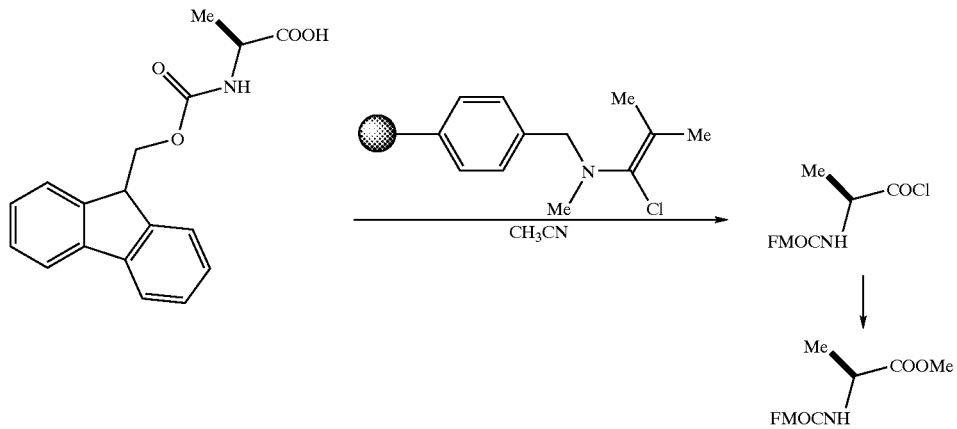

(1-Chlorocarbonyl-ethyl)-carbamic acid 9H-fluoren-9-ylmethyl ester cleanly and completely formed from 2-(9H-fluoren-9-ylmethoxycarbonylamino)-propionic acid within 20 min. $^1$H NMR (CD$_3$CN): δ 7.85 (d, J=7.5 Hz, 2H), 7.68 (d, J=7.1 Hz, 2H), 7.44 (t, J=7.3 Hz, 2H), 7.35 (t, J=7.4 Hz, 2H), 6.44 (br s, 1H), 4.48–4.23 (m, 4H), 1.48 (d, J=7.0 Hz, 3H). $^{13}$C NMR (CD$_3$CN): δ 176.13, 156.08, 144.16, 141.38, 127.95, 127.33, 125.35, 120.21, 66.84, 59.27, 47.15, 15.75.

Methyl 2-(9H-fluoren-9-ylmethoxycarbonylamino)-propionate formed cleanly and completely from the reaction of (1-chlorocarbonyl-ethyl)-carbamic acid 9H-fluoren-9-ylmethyl ester with methanol, to afford a single 254 nm HPLC peak at 10.353 min. $^1$H NMR (CD$_3$CN): δ 7.84 (d, J=7.6 Hz, 2H), 7.68 (d, J=6.8 Hz, 2H), 7.43 (t, J=7.3 Hz, 2H), 7.35 (t, J=7.4 Hz, 2H), 6.07 (br s, 1H), 4.39–4.15 (m, 4H), 3.67 (s, 3H), 1.35 (d, J=7.3 Hz, 3H). $^{13}$C NMR (CD$_3$CN): δ 173.65, 156.07, 144.34, 141.35, 127.91, 127.32, 125.38, 120.19, 66.46, 51.98 (OC̲H$_3$), 49.86, 47.21, 17.05. Calculated C$_{19}$H$_{20}$NO$_4$ (M$^+$+1) exact mass=326.1387. Found 326.1398.

EXAMPLE 5J

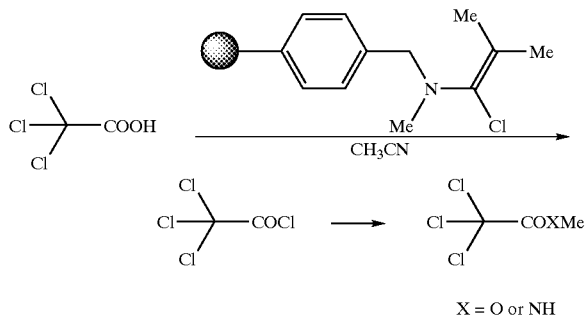

Trichloroacetyl chloride cleanly and completely formed from trichloroacetic acid within 20 min. $^{13}$C NMR (CD$_3$CN): δ 164.09, 93.87. GC-MS showed a single peak in the TIC with a spectrum that was identical to authentic material: m/z 145 (M$^+$−Cl).

Methyl trichloroacetate formed cleanly and completely from the reaction of trichloroacetyl chloride with methanol. $^{13}$C NMR (CD$_3$CN): δ 162.55, 89.75, 56.14 (OC̲H$_3$). GC-MS showed a single peak in the TIC: m/z 141 (M$^+$−Cl).

N-Methyl trichloroacetamide formed cleanly and completely from the reaction of trichloroacetyl chloride with aqueous 40% methylamine. $^{13}$C NMR (CD$_3$CN): δ 162.50, 92.74, 27.41 (NC̲H$_3$). GC-MS showed a single peak in the TIC: m/z 175 (M$^+$). Calculated C$_3$H$_8$Cl$_3$N$_2$O (M+NH$_4^+$) exact masses for chlorine isotopes=192.9697, 194.9667, 196.9638. Found 192.9732, 194.9711, 196.9643.

EXAMPLE 5K

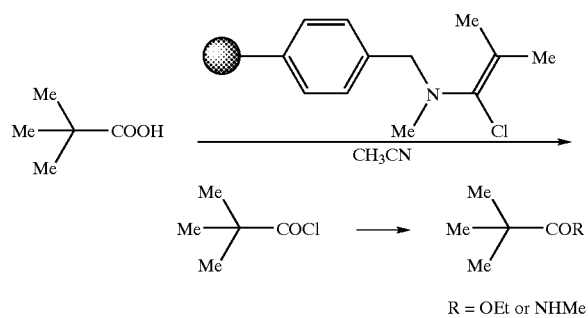

Trimethylacetyl chloride cleanly and completely formed from trimethylacetic acid within 2 hours. $^1$H NMR (CD$_3$CN): δ 1.33 (s, 9H). $^{13}$C NMR (CD$_3$CN): δ 180.62, 49.50, 26.38.

Ethyl trimethylacetate formed cleanly and completely from the reaction of trimethylacetyl chloride with ethanol. $^1$H NMR (CD$_3$CN): δ 4.04 (q, J=7.2 Hz, 2H), 1.18 (t, J=7.2 Hz, 3H), 1.12 (s, 9H). GC-MS showed a single peak in the TIC: m/z 130 (M$^+$).

N-Methyl trimethylacetamide formed cleanly and completely from the reaction of trimethylacetyl chloride with aqueous 40% methylamine. $^1$H NMR (CD$_3$CN): δ 6.29 (br s, 1H), 2.65 (d, J=4.7 Hz, 3H), 1.12 (s, 9H). $^{13}$C NMR (CD$_3$CN): δ 27.00, 25.65 (NCH$_3$).

EXAMPLE 5L

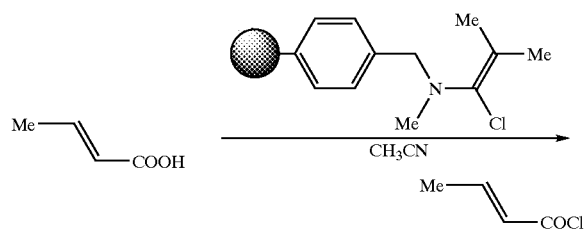

But-2-enoyl chloride cleanly and completely formed from but-2-enoic acid within 20 min, and was identical to authenic compound. $^1$H NMR (CD$_3$CN): δ 7.32 (d of q, J=6.9 Hz, 15.1 Hz, 1H), 6.19 (d of q, J=1.6 Hz, 15.1 Hz, 1H), 1.98 (dd, J=1.6 Hz, 6.9 Hz, 3H). $^{13}$C NMR (CD$_3$CN): δ 154.78, 127.12, 17.77.

EXAMPLE 5M

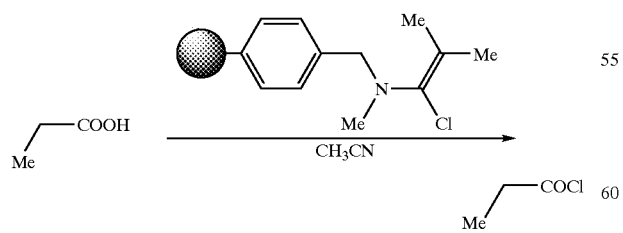

Priopionyl chloride cleanly and completely formed from priopionic acid within 15 min. $^1$H NMR (CD$_3$CN): δ 3.00 (q, J=7.3 Hz, 2H), 1.16 (t, J=7.2 Hz, 3H). $^{13}$C NMR (CD$_3$CN): δ 175.10, 40.87, 8.97.

EXAMPLE 6

General Synthesis of Chlorides from Alcohols Using N-(1-chloro-2-methylprop-1-enyl)-N-methyl aminomethylpolystyrene

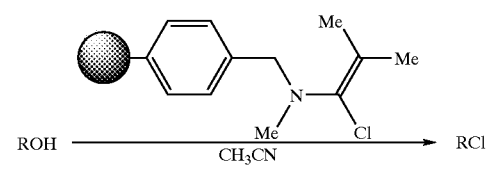

In a dry box, 2 equivalents (per OH group) of N-(1-chloro-2-methylprop-1-enyl)-N-methyl aminomethylpolystyrene was added to a stirred mixture of –0.5–1.0 mmol of an alcohol in CD$_3$CN (3 mL). The resulting reaction mixture was monitored and characterized by $^1$H-NMR, $^{13}$C-NMR, and MS. The following compounds of examples N–R were prepared by these procedures.

EXAMPLE 6N

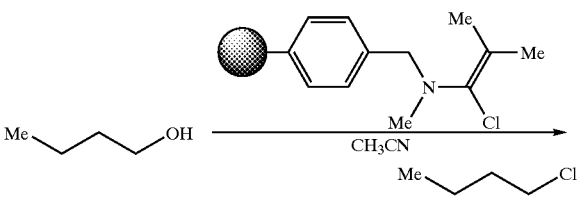

n-Butyl chloride cleanly and completely formed from n-butanol within 15 min. $^1$H NMR (CD$_3$CN): δ 3.60 (t, J=6.7 Hz, 2H), 1.75 (pentet, J=7.0 Hz, 2H), 1.45 (hextet, J=7.4 Hz, 2H), 0.93 (t, J=7.3 Hz, 3H). $^{13}$C NMR (CD$_3$CN): δ 45.11, 34.56, 19.89, 12.74.

EXAMPLE 6O

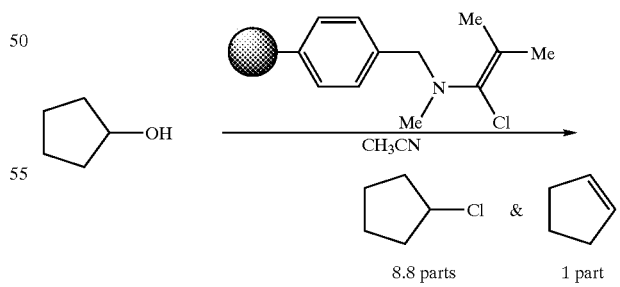

An 8.8 to 1 mixture of cyclopentyl chloride to cyclopentene formed from cyclopentanol within 15 min. Data for cyclopentyl chloride: $^1$H NMR (CD$_3$CN): δ 4.41 (m, 1H), 2.06–1.93 (m, 2H), 1.88–1.74 (m, 4H), 1.68–1.55 (m, 2H). $^{13}$C NMR (CD$_3$CN): δ 62.63, 36.90, 22.81.

EXAMPLE 6P

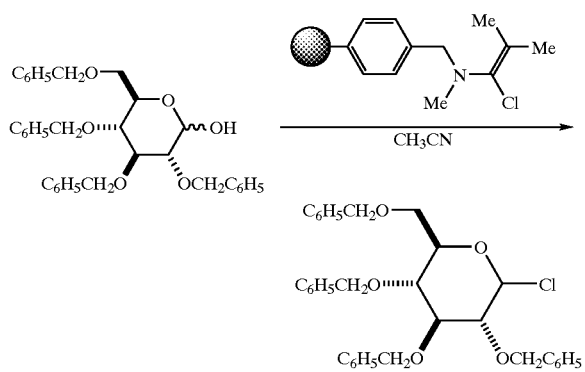

A single anomer of 1-chloro-2,3,4,6-tetra-O-benzyl-D-glucopyranose was cleanly and completely formed from 2,3,4,6-tetra-O-benzyl-D-glucopyranose within 3 hours. $^1$H NMR (CD$_3$CN): δ 7.36–7.16 (m, 20H), 6.32 (d, J=3.6 Hz, 1H), 4.87–4.43 (m, 8H), 4.01–3.95 (m, 1H), 3.89–3.83 (m, 1H), 3.73–3.66 (m, 2H), 3.64–3.55 (m, 2H). $^{13}$C NMR (CD$_3$CN): δ 139.03, 138.64, 138.49, 138.18, 128.60, 128.56, 128.48, 128.46, 128.27, 128.15, 128.12, 128.09, 128.07, 127.85, 127.84, 127.74, 94.31, 81.10, 80.00, 76.75, 75.28, 74.94, 73.87, 73.04, 72.39, 68.45.

EXAMPLE 6Q

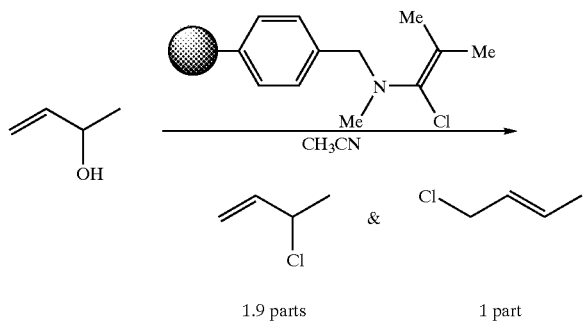

1.9 parts                1 part

A 1.9 to 1 mixture of 3-chloro-1-butene to 1-chloro-2-butene formed from 3-hydroxy-1-butene within 15 min. Data for 3-chloro-1-butene: $^1$H NMR (CD$_3$CN): δ 6.06–5.93 (m, 1H), 5.29 (d, J=16.9 Hz, 1H), 5.12 (d, J=10.2 Hz, 1H), 4.63–4.53 (m, 1H), 1.57 (d, J=6.6 Hz, 3H). $^{13}$C NMR (CD$_3$CN): δ 140.24, 115.25, 58.35, 24.35. Data for 1-chloro-2-butene: $^1$H NMR (CD$_3$CN): δ 5.91–5.60 (m, 2H), 4.08 (d, J=7.0 Hz, 1.72 (d, J=6.2 Hz, 3H). $^{13}$C NMR (CD$_3$CN): δ 131.07, 127.47, 45.54, 16.94.

EXAMPLE 6R

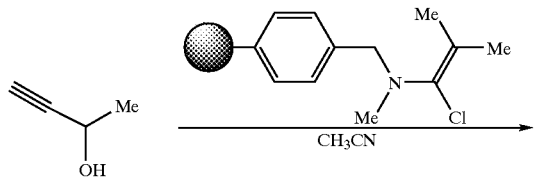

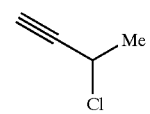

3-Chloro-1-butyne was cleanly and completely formed from 3-hydroxy-1-butyne within 20 min. $^1$H NMR (CD$_3$CN): δ 4.73 (dd, J=2.3 Hz, 6.8 Hz, 1H), 2.88 (d, J=2.4 Hz, 1H), 1.68 (d, J=6.8 Hz, 3H). $^{13}$C NMR (CD$_3$CN): δ 83.20, 74.24, 43.73, 25.98.

EXAMPLE 7

General Synthesis of Silyl Chlorides, Phosphinyl Chlorides, and Sulfonyl Chlorides Using N-(1-chloro-2-methylprop-1-enyl)-N-methyl aminomethylpolystyrene

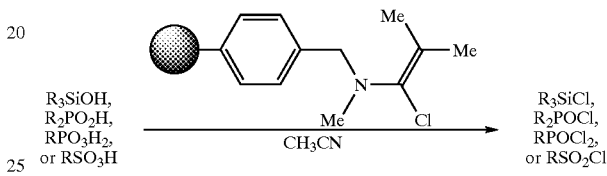

In a dry box, 2 equivalents (per OH group) of N-(1-chloro-2-methylprop-1-enyl)-N-methyl aminomethylpolystyrene was added to a stirred mixture of ~0.5 mmol of an SiOH, PO$_2$H, PO$_3$H$_2$ or SO$_3$H containing compound in CD$_3$CN (3 mL). The resulting reaction mixture was monitored to completion by $^1$H-NMR. Aliquots of the liquid phase containing the corresponding SiCl, POCl, POCl$_2$ or SO$_2$Cl compound were then derivatized by addition to small volumes of methanol or aqueous 40% MeNH$_2$. These reactions were monitored to completion over 1–3 h by $^1$H-NMR and HPLC to form the ester or amide, and then were concentrated under vacuum and characterized. Reverse phase HPLC was carried out on an Agilent 1100 system using a Vydac 4.6×250 mm Protein & Peptide C18 column eluted at 1.2 mL/min with a linear gradient of 20% MeCN:80% H$_2$O to 100% MeCN over a 15 minute period. Both solvents contained 0.1% TFA. The compounds of examples S–W were prepared by these procedures.

EXAMPLE 7S

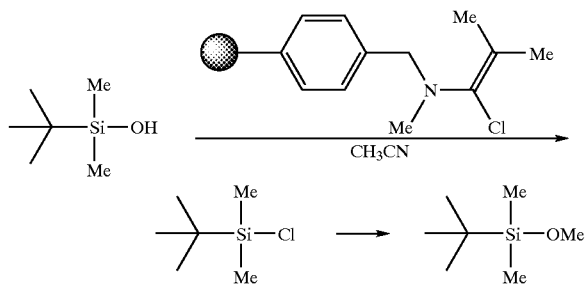

tert-Butyldimethylsilyl chloride was cleanly and completely formed from tert-butyidimethylsilanol in 20 min. $^1$H NMR (CD$_3$CN): δ 0.95 (s, 9H), 0.35 (s, 6H). $^{13}$C NMR (CD$_3$CN): δ 24.78, 18.86, −2.19.

Methyl ether formed cleanly. $^1$H NMR (CD$_3$CN): δ 3.38 (s, 3H), 0.83 (s, 9H), 0.00 (s, 6H). $^{13}$C NMR (CD$_3$CN): δ 50.48 (OCH$_3$), 25.37, 18.08, −6.57.

EXAMPLE 7T

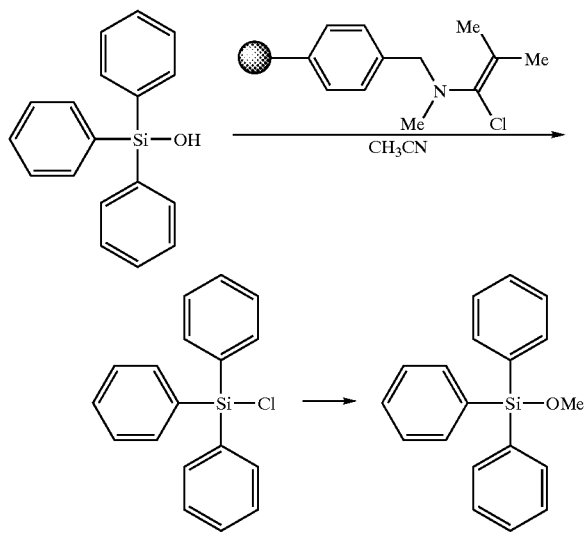

Triphenylsilanol was cleanly converted to triphenylsilyl chloride in 20 min. $^{13}$C NMR (CD$_3$CN): δ 135.10, 132.67, 131.26, 128.55.

Methyl ether formed cleanly. $^1$H NMR (CD$_3$CN): δ 7.55–7.50 (m, 6H), 7.41–7.29 (m, 9H), 3.31 (s, 3H). $^{13}$C NMR (CD$_3$CN): δ 135.15, 133.97, 130.01, 127.77, 48.66 (OCH$_3$). GC-MS showed a single peak in the TIC: m/z 290 (M$^+$).

EXAMPLE 7U

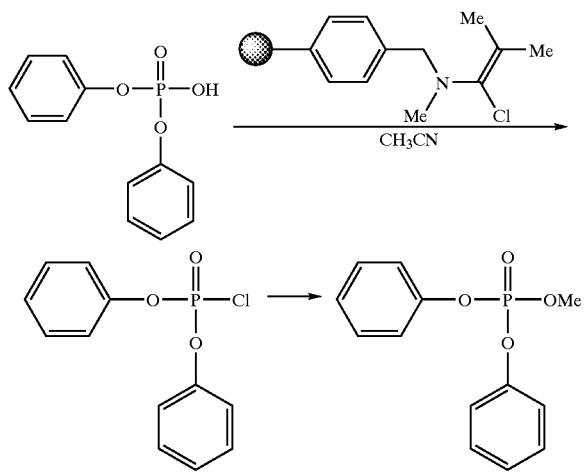

Phosphoric acid diphenyl ester was cleanly and completely converted to phosphorochloridic acid diphenyl ester over 3 hours. $^{31}$P NMR (CD$_3$CN): δ −24.06.

Phosphoric acid methyl ester diphenyl ester formed cleanly and completely from the reaction of phosphorochloridic acid diphenyl ester with methanol, to afford a single 254 nm HPLC peak at 5.036 min. $^1$H NMR (CD$_3$CN): δ 7.43–7.33 (m, 4H), 7.28–7.18 (m, 6H), 3.94 (d, J=11.5 Hz, 3H). $^{31}$P NMR (CD$_3$CN): δ −9.53 Calculated C$_{13}$H$_{14}$O$_4$P (M$^+$+1) exact mass=265.0624. Found 265.0619.

EXAMPLE 7V

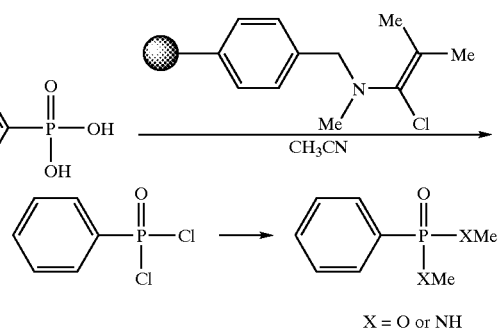

X = O or NH

Phenylphosphoryl dichloride was cleanly and completely formed from phenylphosphonic acid over 8 hours. $^{31}$P NMR (CD$_3$CN): δ 36.56. $^{13}$C NMR (CD$_3$CN): δ 135.25 (d, J=3.8 Hz), 134.36 (d, J=153.4 Hz), 130.36 (d, J=13.9 Hz), 129.68 (d, J=18.3 Hz).

Phenylphosphonic acid dimethyl ester formed cleanly and and completely from the reaction of phenylphosphoryl dichloride with methanol to afford a single 254 nm HPLC peak at 4.932 min. $^1$H NMR (CD$_3$CN): δ 7.81–7.49 (m, 5H), 3.70 (d, J=11.1 Hz, 6H). $^{31}$P NMR (CD$_3$CN): δ 21.73. Calculated C$_8$H$_{12}$O$_3$P (M$^+$+1) exact mass=187.0519. Found 187.0492.

Phenylphosphonic acid bis(N-methylamide) formed cleanly and completely from the reaction of phenylphosphoryl dichloride with gaseous methylamine. $^1$H NMR (CD$_3$CN): δ 7.73–7.65 (m, 2H), 7.46–7.35 (m, 3H), 2.40 (d, J=11.9 Hz, 6H). 31P NMR (CD$_3$CN): δ 23.60. $^{13}$C NMR (CD$_3$CN): δ 131.54 (d, J=9.3 Hz), 130.96 (br), 128.26 (d, J=12.9 Hz), 25.80. Calculated C$_8$H$_{14}$N$_2$O$_2$P (M$^+$+1) exact mass=185.0838. Found 185.0838.

EXAMPLE 7W

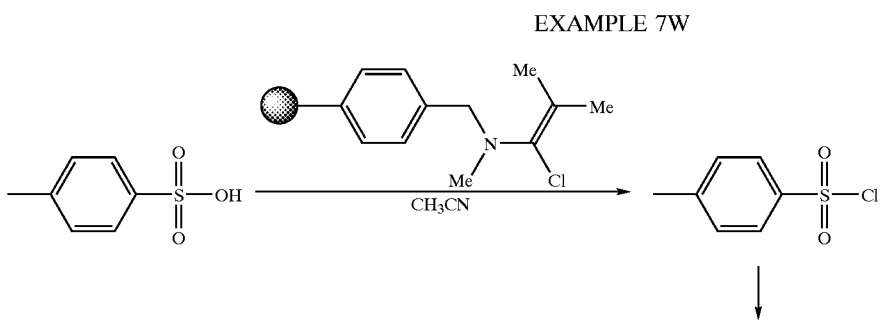

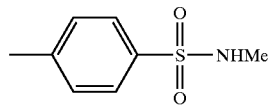

p-Toluene sulfonyl chloride was cleanly and completely formed from p-toluene sulfonic acid monohydrate over 1 hour. $^1$H NMR (CD$_3$CN): δ 7.97 (d, J=8.5 Hz, 2H), 7.53 (d, J=8.2 Hz, 2H), 2.49 (s, 3H). $^{13}$C NMR (CD$_3$CN): δ 148.12, 130.78, 127.13, 21.07.

p-Toluene sulfonamide formed cleanly from the reaction of p-toluene sulfonyl chloride with aqueous 40% methylamine to afford a single 254 nm HPLC peak at 6.089 min. $^1$H NMR (CD$_3$CN): δ 7.74 (d, J=8.2 Hz, 2H), 7.41 (d, J=8.1 Hz, 2H), 3.67 (s, 3H), 2.41 (s, 3H). Calculated C$_8$H$_{12}$NO$_2$S (M$^+$+1) exact mass=186.0583. Found 186.0610.

EXAMPLE 8

Synthesis of N-tert-butyl Benzamide using N-(1-chloro-2-methylprop-1-enyl)-N-methyl aminomethylpolystyrene

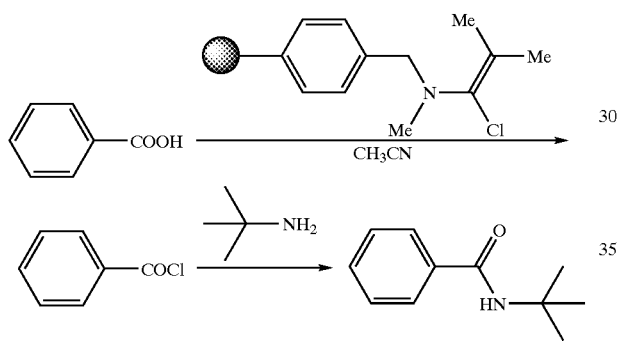

A mixture of benzoic acid (1.00 g, 8.2 mmol) and N-(1-chloro-2-methylprop-1-enyl)-N-methyl aminomethylpolystyrene (1.55 mequiv/g, 8.00 g, 12.4 mequiv) in anhydrous acetonitrile (25 mL) was stirred at ambient temperature with no significant exotherm. Benzoyl chloride was cleanly formed over 10 minutes. $^1$H NMR (CD$_3$CN): δ 8.17–8.12 (m, 2H), 7.83–7.76 (m, 1H), 7.64–7.57 (m, 2H). GC-MS m/z (M$^+$).

The reaction mixture was then filtered under a nitrogen atmosphere and the resin washed with 25 mL of dry acetonitrile. The combined acetonitrile filtrates containing the benzoyl chloride were added to a solution of tert-butylamine (2.58 mL, 24.6 mmol) in CH$_2$Cl$_2$ (20 mL). After 10 minutes the reaction was diluted with CH$_2$Cl$_2$ and washed with dilute aqueous HCl, followed with dilute aqueous NaOH. The CH$_2$Cl$_2$ solution was dried (MgSO$_4$) and concentrated to afford an 82% yield (1.19 g) of tert-butyl benzamide as a white solid. $^1$H NMR (CD$_3$CN): δ 7.74–7.68 (m, 2H), 7.50–7.36 (m, 3H), 5.93 (br s, 1H), 1.47 (s, 9H). GC-MS m/z 177 (M+).

EXAMPLE 9

Synthesis of 4-[(4-tert-butoxycarbonylamino-1-methyl-1H-imidazole-2-carbonyl)-amino]-1-methyl-1H-imidazole-2-carboxylic acid methyl ester using N-(1-chloro-2-methylprop-1-enyl)-N-methyl aminomethylpolystyrene

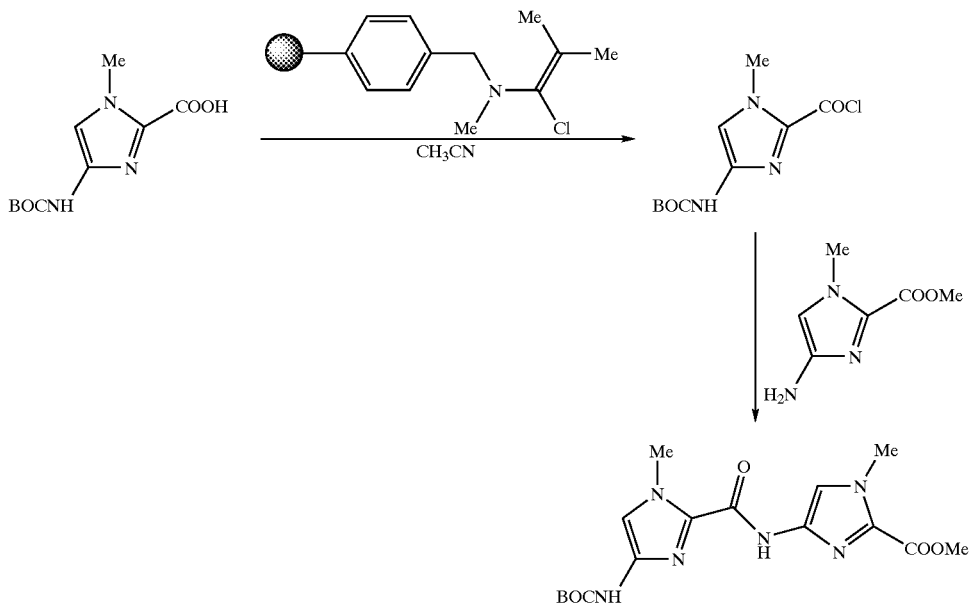

A mixture of 4-tert-butoxycarbonylamino-1-methyl-1H-imidazole-2-carboxylic acid (1.30 g, 5.40 mmol) and N-(1-chloro-2-methylprop-1-enyl)-N-methyl aminomethylpolystyrene (1.55 mequiv/g, 6.96 g, 10.77 mequiv) in anhydrous acetonitrile (20 mL) was stirred at ambient temperature. Over 15 minutes, all of the BOCNH-Im-COOH dissolved and was converted to the corresponding acid chloride.

The reaction mixture was then filtered under a nitrogen atmosphere and the resin washed with 20 mL of dry acetonitrile. The acetonitrile filtrates containing the acid chloride were combined and added dropwise to a vigorously stirred 2-phase mixture of a solution of 4-amino-1-methyl-1H-imidazole-2-carboxylic acid methyl ester (643 mg, 4.15 mmol) in $CH_2Cl_2$ (20 mL) and a solution of $Na_2CO_3$ (572 mg, 5.40 mmol) in $H_2O$ (20 mL). The resulting reaction mixture was stirred for 5 minutes, and then was diluted with $CH_2Cl_2$ and $H_2O$. The $CH_2Cl_2$ solution was isolated, dried ($MgSO_4$), and concentrated to afford a quantitative yield (1.64 g) of 4-[(4-tert-butoxycarbonylamino-1-methyl-1H-imidazole-2-carbonyl)-amino]-1-methyl-1H-imidazole-2-carboxylic acid methyl ester as a very pure off-white solid. Reverse phase HPLC of this material was carried out on an Agilent 1100 system using a Vydac 4.6×250 mm Protein & Peptide C18 column eluted at 1.2 mL/min with a linear gradient of 20% MeCN:80% $H_2O$ to 40% MeCN:60% $H_2O$ over a 15 minute period. Both solvents contained 0.1% TFA. A single 304 nm HPLC peak eluted at 12.223 minutes. $^1$H NMR ($CD_3CN$): δ 7.56 (s, 1H), 7.14 (br s, 1H), 4.01 (s, 3H), 4.00 (s, 3H), 3.90 (s, 3H), 1.51 (s, 9H).

EXAMPLE 10

Synthesis of 1-methyl-4-{[1-methyl-4-({1-methyl-4-[(1-methyl-1H-imidazole-2-carbonyl)-amino]-1H-imidazole-2-carbonyl}-amino)-1H-imidazole-2-carbonyl]-amino}-1H-pyrrole-2-carboxylic acid methyl ester using N-(1-chloro-2-methylprop-1-enyl)-N-methyl aminomethylpolystyrene

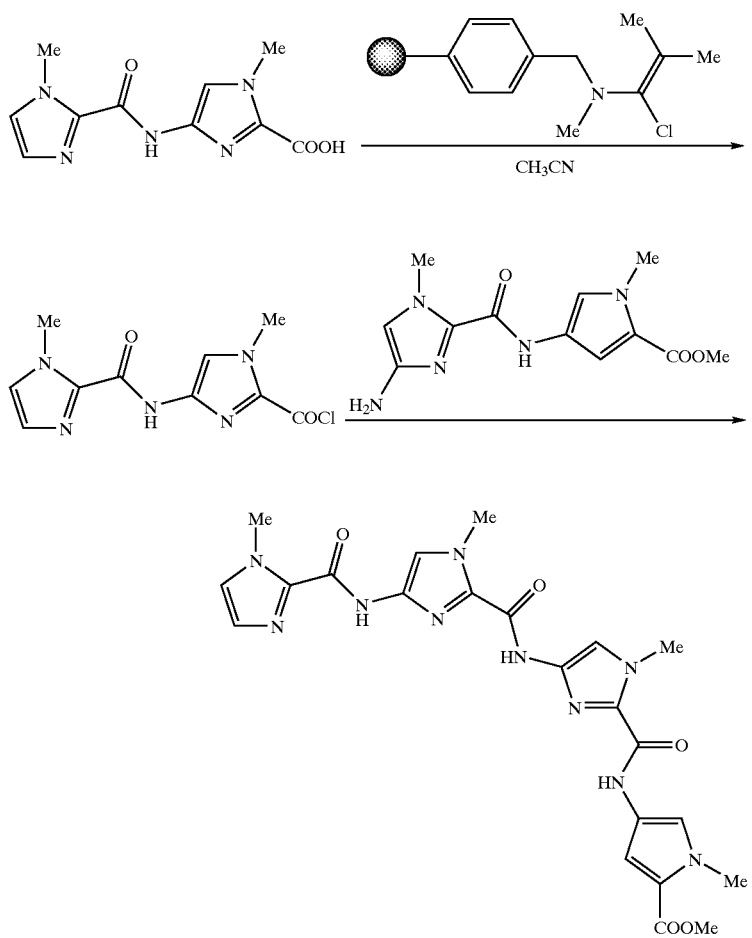

Trimethylsilyl triflate (150 μL, 0.81 mmol) was added in a single portion to a mixture of 1-methyl-4-[(1-methyl-1H-imidazole-2-carbonyl)-amino]-1H-imidazole-2-carboxylic acid (200 mg, 0.80 mmol) in anhydrous acetonitrile (8.00 mL). The solution which formed within a few moments was transferred to solid N-(1-chloro-2-methylprop-1-enyl)-N-methyl aminomethylpolystyrene (1.55 mequiv/g, 1.04 g, 1.61 mequiv). After stirring at ambient temperature for 10 minutes, an equal volume of anhydrous CHCl₃ (stabilized with amylenes) was added and the mixture was filtered in an inert atmosphere. The resin was washed with an additional 10 mL of anhydrous CHCl₃ (stabilized with amylenes), and the combined filtrates containing the 1-methyl-4-[(1-methyl-1H-imidazole-2-carbonyl)-amino]-1H-imidazole-2-carbonyl chloride were added dropwise to a vigorously stirred 2-phase mixture of a solution of 4-[(4-amino-1-methyl-1H-imidazole-2-carbonyl)-amino]-1-methyl-1H-pyrrole-2-carboxylic acid methyl ester (171 mg, 0.62 mmol) in CHCl₃ (10 mL), and a solution of Na₂CO₃ (170 mg, 1.60 mmol) in H₂O (5 mL). The resulting reaction mixture was stirred for 5 minutes, and then was diluted with CHCl₃ and H₂O. The CHCl₃ solution was isolated, dried (MgSO₄), and concentrated to afford a 59% yield (240 mg) of 1-methyl-4-{[1-methyl-4-({1-methyl-4-[(1-methyl-1H-imidazole-2-carbonyl)-amino]-1H-imidazole-2-carbonyl}-amino)-1H-imidazole-2-carbonyl]-amino}-1H-pyrrole-2-carboxylic acid methyl ester as a very pure off-white solid. Reverse phase HPLC of this material was carried out on an Agilent 1100 system using a Vydac 4.6×250 mm Protein & Peptide C18 column eluted at 1.2 mL/min with a linear gradient of 20% MeCN:80% H₂O to 40% MeCN:60% H₂O over a 15 minute period. Both solvents contained 0.1% TFA. A single 304 nm HPLC peak eluted at 10.847 minutes. ¹H NMR (CD₃CN plus TFA): δ 10.90 (s, 1H), 10.71 (s, 1H), 9.49 (s, 1H), 7.85 (s, 1H), 7.76 (s, 1H), 7.65 (m, 2H), 7.46 (d, J=1.8 Hz, 1H), 6.92 (d, J=1.9 Hz, 1H), 4.15 (s, 3H), 4.12 (s, 3H), 4.11 (s, 3H), 3.92 (s, 3H), 3.80 (s, 3H).

What is claimed is:

1. A process for the preparation of an α-haloenamine, the process comprising combining a tertiary amide with a pentavalent phosphorous halide in a solvent to form an α-haloiminium salt and converting the α-haloiminium salt to the α-haloenamine with a base, the pentavalent phosphorous halide having the formula $$P(X)_2(Z)_3$$

wherein each X is independently a halogen atom and each Z is independently a halogen atom or a carbon atom which is part of a substituted or unsubstituted hydrocarbyl radical, and further wherein the tertiary amide is covalently linked to a support which enables physical separation of the α-haloenamine from a liquid composition.

2. The process of claim 1 wherein the base is a tertiary amine.

3. The process of claim 1 wherein the base is triethylamine.

4. The process of claim 1 wherein the α-haloenamine is an α-chloroenamine, α-bromoenamine, α-fluoroenamine or α-iodoenamine.

5. The process of claim 2 wherein the pentavalent phosphorous halide is phosphorous pentachloride or phosphorous pentabromide.

6. The process of claim 5 wherein the pentavalent phosphorous halide is phosphorous pentachloride.

7. The process of claim 1 wherein the α-haloenamine is α-chloroenamine, α-bromoenamine, or α-iodoenamine and the process comprises combining a tertiary amide with the pentavalent phosphorous halide.

8. The process of claim 1 wherein the process comprises combining a tertiary amide with the pentavalent phosphorous halide to form an α-chloroenamine and displacing the chloride of the α-chloroenamine with bromide, fluoride or iodide.

9. The process of claim 1 wherein the solvent comprises acetonitrile.

10. The process of claim 1 wherein the support is inorganic, the inorganic support being selected from the group consisting of silicates, quartz and aluminum.

11. The process of claim 1 wherein the support is polymeric.

12. The process of claim 1 wherein the tertiary amide is a tertiary amide reagent having the formula:

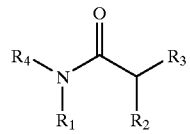

wherein

R₁ and R₄ are independently hydrocarbyl, substituted hydrocarbyl, hydrocarbyloxy, or substituted hydrocarbyloxy; and R₂ and R₃ are independently hydrogen, hydrocarbyl, substituted hydrocarbyl, hydrocarbylthio, substituted hydrocarbylthio, hydrocarbylcarbonyl, substituted hydrocarbylcarbonyl, hydrocarbyloxycarbonyl, substituted hydrocarbyloxycarbonyl phosphinyl, thiophosphinyl, sulfinyl, sulfonyl, halo, cyano, or nitro, provided at least one of R₁, R₂, R₃ and R₄ comprises a support which enables physical separation of the tertiary amide from a liquid mixture.

13. The process of claim 12 wherein three of R₁, R₂, R₃ and R₄ are alkyl.

14. The process of claim 12 wherein two of R₁, R₂, R₃ and R₄ in combination define a carbocyclic or heterocyclo ring.

15. The process of claim 12 wherein three of R₁, R₂, R₃ and R₄ are alkyl and the other is covalently linked to a polymeric support.

16. The process of claim 12 wherein the tertiary amide reagent is poly(N,N-disubstituted acrylamide).

17. The process of claim 12 wherein the tertiary amide reagent is a polymer having N,N-disubstituted amide moieties.

18. The process of claim 12 wherein the tertiary amide reagent is a polymer having N,N-dialkyl substituted amide moieties.

19. The process of claim 12 wherein the amide moiety of the tertiary amide reagent is covalently attached to the phenyl ring of a polystyrene polymer or copolymer through one of R¹, R², R³ or R⁴.

* * * * *